(12) United States Patent
Clauson et al.

(10) Patent No.: US 11,413,188 B2
(45) Date of Patent: Aug. 16, 2022

(54) DEVICES AND METHODS FOR CUTTING A LENS IN AN EYE

(71) Applicant: Carl Zeiss Meditec Cataract Technology Inc., Reno, NV (US)

(72) Inventors: Luke W. Clauson, Reno, NV (US); Scott Chamness, Reno, NV (US); Michael Schaller, Reno, NV (US); Jens Hoekendijk, Reno, NV (US)

(73) Assignee: Carl Zeiss Meditec Cataract Technology Inc., Reno, NV (US)

( * ) Notice: Subject to any disclaimer, the term of this patent is extended or adjusted under 35 U.S.C. 154(b) by 469 days.

(21) Appl. No.: 16/345,182

(22) PCT Filed: Oct. 25, 2017

(86) PCT No.: PCT/US2017/058330
§ 371 (c)(1),
(2) Date: Apr. 25, 2019

(87) PCT Pub. No.: WO2018/081295
PCT Pub. Date: May 3, 2018

(65) Prior Publication Data
US 2019/0282402 A1  Sep. 19, 2019

Related U.S. Application Data

(60) Provisional application No. 62/413,424, filed on Oct. 26, 2016.

(51) Int. Cl.
*A61F 9/007* (2006.01)
*A61B 17/3205* (2006.01)
(Continued)

(52) U.S. Cl.
CPC .......... *A61F 9/00763* (2013.01); *A61B 17/32* (2013.01); *A61B 17/3205* (2013.01);
(Continued)

(58) Field of Classification Search
CPC .............. A61F 9/00754; A61F 9/00736; A61F 9/00763; A61F 9/007–0079;
(Continued)

(56) References Cited

U.S. PATENT DOCUMENTS 1,891,054 A  12/1932  Pitman
3,882,872 A  5/1975  Douvas et al.
(Continued)

FOREIGN PATENT DOCUMENTS

CN  101495063 A  7/2009
CN  104736076 A  6/2015
(Continued)

OTHER PUBLICATIONS

U.S. Appl. No. 14/894,299, filed Nov. 25, 2015, US 2016-0166432.
(Continued)

*Primary Examiner* — Katherine H Schwiker
(74) *Attorney, Agent, or Firm* — Mintz Levin Cohn Ferris Glovsky and Popeo, P.C.

(57) ABSTRACT

Devices and methods for cutting a lens in the eye are provided with a specific application being for cutting a lens while contained within the capsular bag. The device has an elongate element which forms a loop. The loop is advanced into a space between the lens and the capsular bag. The device may be used with, or incorporated into, fluid handling devices such as irrigation and aspiration devices and phacoemulsification hand pieces and disposables.

16 Claims, 22 Drawing Sheets

(51) Int. Cl.
*A61F 9/008* (2006.01)
*A61B 17/32* (2006.01)

(52) U.S. Cl.
CPC ........ *A61B 17/32056* (2013.01); *A61F 9/008* (2013.01); *A61F 9/00736* (2013.01); *A61B 2217/005* (2013.01); *A61B 2217/007* (2013.01)

(58) Field of Classification Search
CPC ........ A61B 17/32056; A61B 17/22004; A61B 2217/005; A61B 2217/007; A61B 2017/1407; A61B 2017/141
See application file for complete search history.

(56) References Cited

U.S. PATENT DOCUMENTS

| | | | |
|---|---|---|---|
| 3,908,661 A | 9/1975 | Kramer | |
| 3,973,568 A | 8/1976 | Iglesias | |
| 4,331,130 A * | 5/1982 | Lewicky | A61F 9/00736 604/23 |
| 4,367,744 A | 1/1983 | Sole | |
| 4,538,611 A | 9/1985 | Kelman | |
| 4,693,245 A | 9/1987 | Pao | |
| 4,732,150 A | 3/1988 | Keener, Jr. | |
| 4,766,897 A | 8/1988 | Smirmaul | |
| 4,791,924 A | 12/1988 | Kelman | |
| 4,869,716 A | 9/1989 | Smirmaul | |
| 4,888,015 A | 12/1989 | Domino | |
| 4,950,272 A | 8/1990 | Smirmaul | |
| 4,955,887 A | 9/1990 | Zirm | |
| 4,960,418 A | 10/1990 | Tennant | |
| 5,123,906 A | 6/1992 | Kelman | |
| 5,147,369 A | 9/1992 | Wagner | |
| 5,156,607 A | 10/1992 | Kansas | |
| 5,171,314 A | 12/1992 | Dulebohn | |
| 5,201,741 A | 4/1993 | Dulebohn | |
| 5,222,959 A | 6/1993 | Anis | |
| 5,222,960 A | 6/1993 | Poley | |
| 5,242,449 A | 9/1993 | Zaleski | |
| 5,437,678 A | 8/1995 | Sorensen | |
| 5,728,117 A | 3/1998 | Lash | |
| 6,117,149 A | 9/2000 | Sorensen et al. | |
| 6,120,496 A | 9/2000 | Whayne et al. | |
| 6,379,370 B1 | 4/2002 | Feinsod | |
| 6,551,326 B1 | 4/2003 | Van Heugten et al. | |
| 6,554,843 B1 | 4/2003 | Ou | |
| 6,743,228 B2 | 6/2004 | Lee et al. | |
| 7,632,294 B2 | 12/2009 | Milbodker et al. | |
| 7,867,163 B2 | 1/2011 | Chin et al. | |
| 8,157,797 B2 | 4/2012 | Boukhny et al. | |
| 8,814,854 B2 | 8/2014 | Jia et al. | |
| 9,381,033 B2 | 7/2016 | Guo | |
| 9,629,747 B2 | 4/2017 | Clauson et al. | |
| 10,292,862 B1 | 5/2019 | Mackool | |
| 2002/0019594 A1 | 2/2002 | McClellan et al. | |
| 2003/0074008 A1 | 4/2003 | Ou | |
| 2004/0092982 A1 | 5/2004 | Sheffer | |
| 2004/0116950 A1 | 6/2004 | Eibschitz-Tsimhoni | |
| 2004/0199159 A1 | 10/2004 | Lee et al. | |
| 2004/0220564 A1 | 11/2004 | Ho et al. | |
| 2004/0220604 A1 * | 11/2004 | Fogarty | A61B 17/0218 606/190 |
| 2004/0243142 A1 | 12/2004 | Siepser | |
| 2008/0086148 A1 | 4/2008 | Baker et al. | |
| 2009/0054904 A1 | 2/2009 | Holmen | |
| 2009/0204135 A1 | 8/2009 | Cote | |
| 2009/0216225 A1 | 8/2009 | Ben-Nun | |
| 2010/0094278 A1 | 4/2010 | Jia et al. | |
| 2010/0312232 A1 | 12/2010 | Jia et al. | |
| 2010/0312252 A1 | 12/2010 | Jia et al. | |
| 2011/0282335 A1 | 11/2011 | Jia et al. | |
| 2012/0172905 A1 | 7/2012 | Lee Shee et al. | |
| 2013/0023894 A1 | 1/2013 | Saleh | |
| 2014/0074011 A1 | 3/2014 | Charles | |
| 2014/0114335 A1* | 4/2014 | Banko | A61B 17/3421 606/169 |
| 2014/0180396 A1 | 6/2014 | Pike et al. | |
| 2014/0378988 A1 | 12/2014 | Raybin et al. | |
| 2015/0005578 A1 | 1/2015 | Jorgensen et al. | |
| 2015/0257927 A1 | 9/2015 | Olson | |
| 2015/0297407 A1 | 10/2015 | Saimovici | |
| 2015/0305934 A1 | 10/2015 | Joo et al. | |
| 2015/0335393 A1 | 11/2015 | Ciulla et al. | |
| 2016/0030241 A1 | 2/2016 | Siepser | |
| 2016/0067091 A1 | 3/2016 | Wells et al. | |
| 2016/0074220 A1 | 3/2016 | Ianchulev et al. | |
| 2016/0166432 A1 | 6/2016 | Kahook et al. | |
| 2016/0346121 A1 | 12/2016 | Ianchulev et al. | |
| 2017/0143341 A1 | 5/2017 | Belson et al. | |
| 2017/0231647 A1 | 8/2017 | Saunders et al. | |
| 2017/0312125 A1 | 11/2017 | Clauson et al. | |
| 2018/0036171 A1 | 2/2018 | Clauson et al. | |
| 2018/0064578 A1 | 3/2018 | Clauson et al. | |
| 2018/0132998 A1 | 5/2018 | Page | |
| 2018/0318132 A1 | 11/2018 | Clauson et al. | |
| 2018/0318133 A1 | 11/2018 | Clauson et al. | |
| 2019/0133825 A1 | 5/2019 | Clauson et al. | |
| 2019/0151149 A1 | 5/2019 | Clauson et al. | |
| 2019/0183681 A1 | 6/2019 | Schaller et al. | |
| 2019/0336337 A1 | 11/2019 | MacKool | |
| 2019/0336338 A1 | 11/2019 | MacKool | |
| 2019/0365567 A1 | 12/2019 | Balkenbush et al. | |
| 2020/0289319 A1 | 9/2020 | Carter et al. | |

FOREIGN PATENT DOCUMENTS

| | | |
|---|---|---|
| EP | 0 994 281 A2 | 4/2000 |
| EP | 0870486 B1 | 11/2005 |
| FR | 2655836 A1 | 6/1991 |
| GB | 2536365 A | 9/2016 |
| GB | 2532596 B | 5/2017 |
| JP | 3069723 U | 6/2000 |
| RU | 2068251 C1 | 10/1996 |
| RU | 2014124946 A | 12/2015 |
| WO | WO-99/59510 A1 | 11/1999 |
| WO | WO-2006/068650 A1 | 6/2006 |
| WO | WO-2007/011302 A1 | 1/2007 |
| WO | WO-2012/048348 A1 | 4/2012 |
| WO | WO-2016/036406 A1 | 3/2016 |
| WO | WO-2017/143272 A2 | 8/2017 |
| WO | WO-2018/217579 A1 | 11/2018 |

OTHER PUBLICATIONS

U.S. Appl. No. 15/418,764, filed Jan. 29, 2017, US 2018-0064578.
U.S. Appl. No. 15/460,256, filed Mar. 16, 2017, US 2017-0312125.
U.S. Appl. No. 15/688,024, filed Aug. 28, 2017, US 2018-0036171.
U.S. Appl. No. 16/221,239, filed Dec. 14, 2018, US 2019-0183681.
U.S. Appl. No. 16/240,186, filed Jan. 4, 2019, US 2019-0133825.
U.S. Appl. No. 16/257,533, filed Jan. 25, 2019, US 2019-0151149.
PCT/US2018/033464, May 18, 2018, WO 2018/217579.
"Phaco-Section by Wire Snare—A New Technique of Non-Phaco Stitchless Surgery for Suprahard Cataracts." Basak, Samar K. (Jan. 30, 2013 published). URL: https://www.youtube.com/watch?v=CP8jrVb8qrg Retreived from YouTube.com. May 28, 2019. 1 page.
Bhattacharya, Debasish. (2009) "Nuclear management in manual small incision cataract surgery by snare technique." Indian J Ophthalmol. Jan.-Feb. 2009; 57 (1): 27-29.
Blumenthal, Michael et al. (1992) "Small-Incision Manual Extracapsular Cataract Extraction Using Selective Hydrodissection." Ophthalmic Surg., Oct. 1992; 23(10):699-701.
"General Catalog for Inami Surgical Instrument." Inami & Co., Ltd. (1998) 2 pages. [English language translation].
"General Catalog for Inami Surgical Instrument." Inami & Co., Ltd. (1998) 2 pages. [Japanese language].
U.S. Appl. No. 15/970,439, filed May 3, 2018, US 2018-0318132.
U.S. Appl. No. 16/404,252, filed May 6, 2019, US 2019-0254872.
U.S. Appl. No. 16/431,560, filed Jun. 4, 2019, US 2019-0365567.
U.S. Appl. No. 16/436,648, filed Jun. 10, 2019, US 2019-0321223.
U.S. Appl. No. 16/577,418, filed Sep. 20, 2019, US 2020-0022841.

(56) References Cited

OTHER PUBLICATIONS

U.S. Appl. No. 16/667,030, filed Oct. 29, 2019, US 2020-0060875.
U.S. Appl. No. 16/690,881, filed Nov. 21, 2019, US 2020-0197222.
U.S. Appl. No. 16/778,755, filed Jan. 31, 2020, US 2020-0289319.
U.S. Appl. No. 16/811,786, filed Mar. 6, 2020, US 2020-0306083.
U.S. Appl. No. 16/875,421, filed May 15, 2020, US 2020-0383833.
U.S. Appl. No. 16/875,426, filed May 15, 2020, US 2020-0360185.
U.S. Appl. No. 17/177,017, filed Feb. 16, 2021, US 2021-0161712.

* cited by examiner

A-A

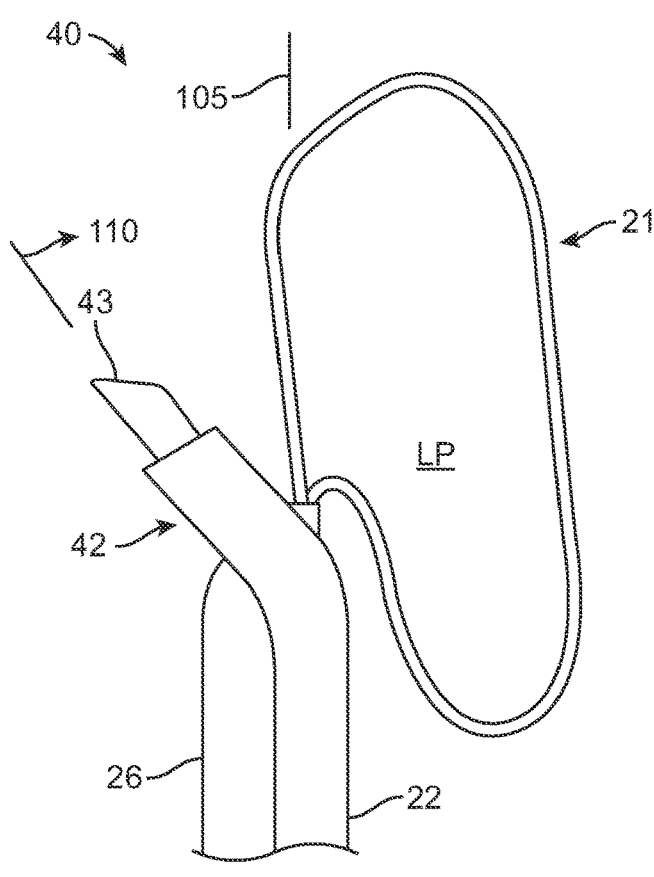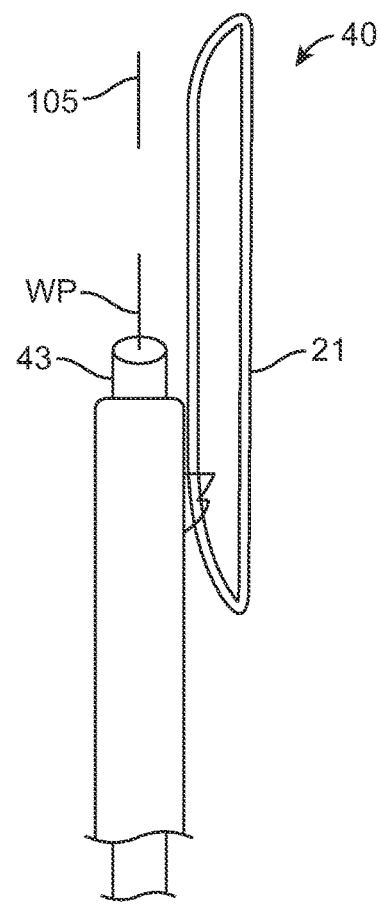
FIG. 16A
FIG. 16B
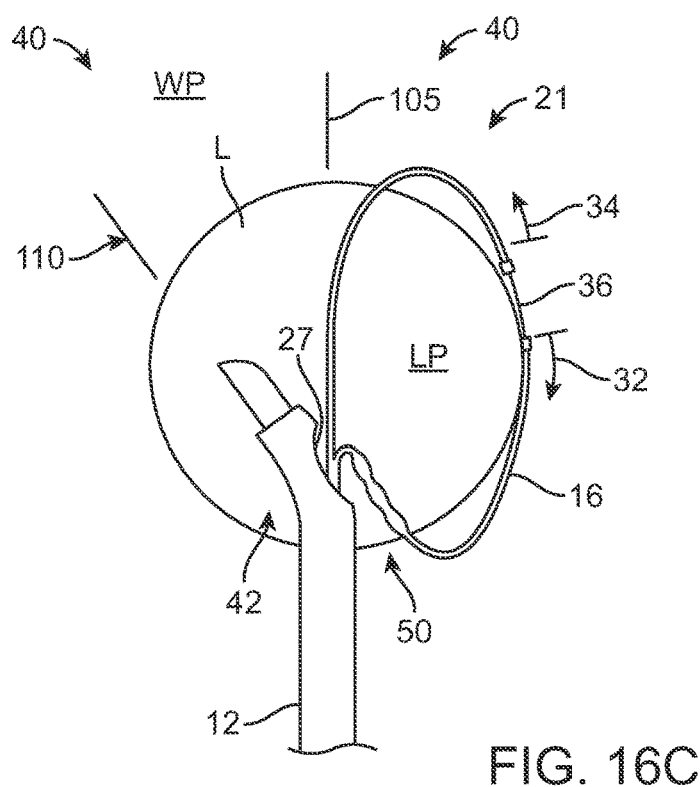
FIG. 16C

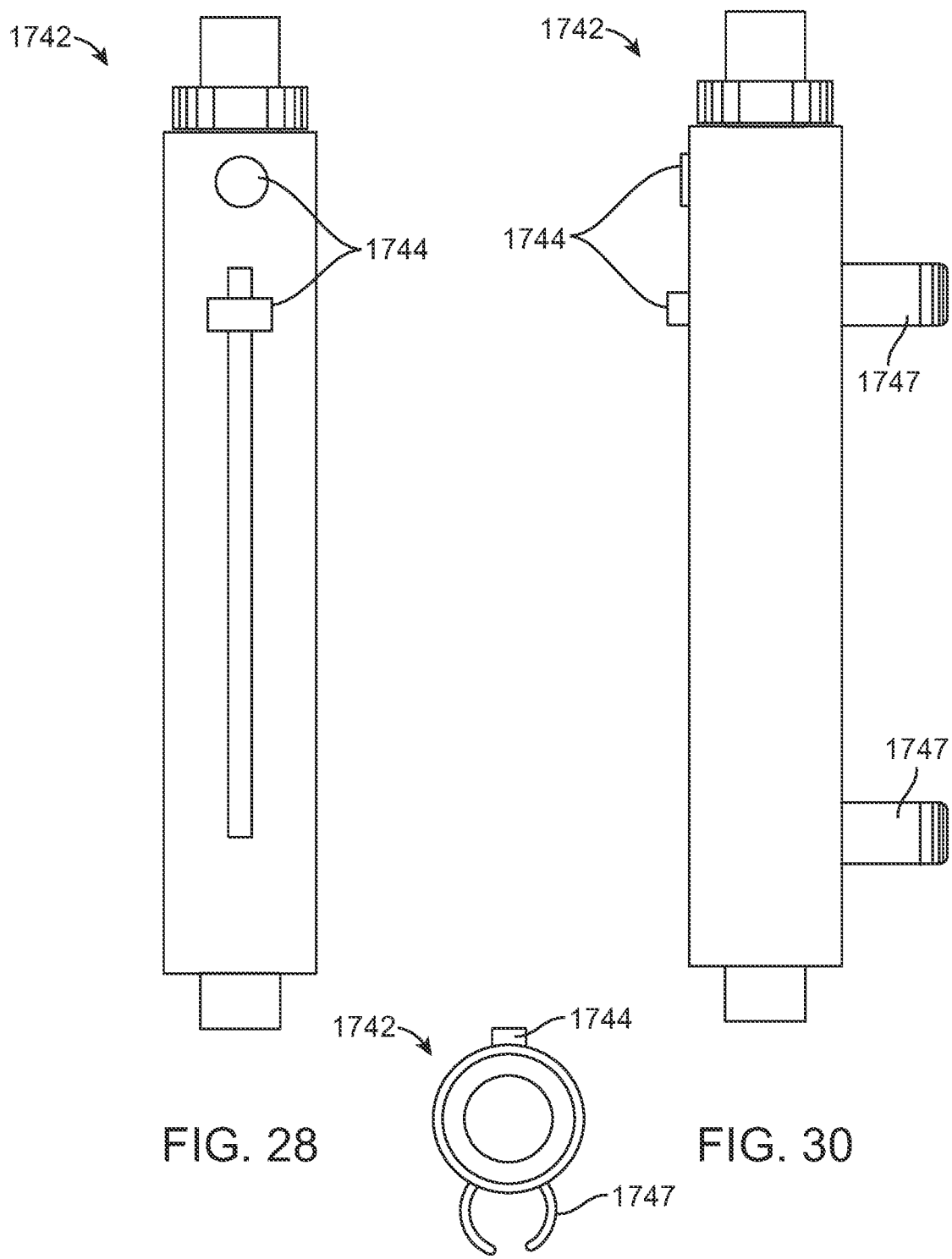

DEVICES AND METHODS FOR CUTTING A LENS IN AN EYE

CROSS-REFERENCE TO RELATED APPLICATIONS

This application is a 371 U.S. National Phase Application of co-pending PCT Application Serial No. PCT/US2017/058330, filed on Oct. 25, 2017, which claims the benefit of priority to U.S. Provisional Application No. 62/413,424, filed Oct. 26, 2016, entitled "Devices and Methods for Cutting a Lens in an Eye," the entire contents of which are incorporated by reference herein in their entirety for all purposes.

FIELD

The present technology relates generally to medical devices and methods, and more particularly, to methods and devices for cutting a lens in an eye.

BACKGROUND

Described herein are methods and devices for cutting a lens in an eye, which may be useful in performing cataract surgery. The devices and methods described are particularly useful for endocapsular lens cutting (inside the capsular bag). It should be appreciated the devices described herein may be useful for cutting a lens outside the capsular bag as well.

Cutting and removal of the lens can be a time-consuming and difficult part of a cataract procedure. In particular, the lens is contained in a delicate capsular bag which can be easily damaged. Lens cutting devices and methods are described in U.S. Pat. No. 9,629,747, filed Mar. 17, 2016, DEVICES AND METHODS FOR CUTTING LENTICULAR TISSUE, which is hereby incorporated by reference in its entirety. The devices described have an elongate element which expands to form a loop capable of being positioned around the lens and capable of being reduced in size to cut the lens once the loop is positioned around the lens. The loop is maneuvered around the lens in a controlled manner to prevent damage to the capsular bag surrounding the lens.

SUMMARY

In a first aspect, described is a method of cutting a lens in a cataract procedure. The method includes introducing a lens cutting device into an eye. The lens cutting device has an elongate element coupled to a support shaft. The elongate element has a first end and a second end, at least one of the first end and the second end being movable relative to the other to change a size of a loop formed at least in part by the elongate element. The loop is movable from a collapsed position to an expanded position. The loop is in the collapsed position during the introducing step. The method further includes positioning the loop around the lens with the loop in the expanded position and cutting the lens by reducing a size of the loop after the positioning step.

The positioning step can be carried out with the elongate element being advanced between a capsular bag and the lens while the lens is positioned in the capsular bag. The method can further include releasing at least one of the first end and the second end after the cutting step; and withdrawing the at least one end from the eye after the cutting and releasing steps. The positioning step can be carried out with the elongate element having an elbow at the first end, the elbow extending from the support shaft when the loop is in the expanded position. The positioning step can be carried out with the elbow extending proximally from the support shaft when the loop is in the expanded position. The positioning step can be carried out with the loop generally defining a loop plane in the expanded position, the elbow being at least twice as flexible in bending for a force applied to a tip of the elbow and lying in the loop plane compared to a transverse force applied to the tip of the elbow and directed transverse to the loop plane. The introducing step can be carried out with the elbow having a living hinge. The introducing step can be carried out with the living hinge being a crimped portion. The introducing step can be carried out with the elbow being integrally formed with the support shaft. The introducing step can be carried out with the elbow being made of a polymer.

The method can further include rotating the support shaft to deflect the elbow toward the support shaft by engaging the lens when rotating, the elbow moving to a position between the support shaft and lens before the cutting step. The positioning step can be carried out with the elbow having an unbiased position relative to the support shaft when the loop is in the expanded position, the elbow having a tip having an orientation at the tip which is 90-180 degrees from a distal orientation of the support shaft when the loop is in the expanded position, the distal orientation being a direction of a longitudinal axis of the support shaft at a distal end of the support shaft. The introducing step can be carried out with the first end of the elongate element having an elbow, the elbow having an unbiased shape which directs the elbow proximally relative to the support shaft when the loop is in the expanded position. The introducing step can be carried out with the elongate element being folded at a flexible portion when the loop is in the collapsed position. The introducing step can be carried out with the flexible portion being folded in a U-shape with a first side of the U-shape extending to the first end and a second side of the U-shape extending to the second end. The introducing step can be carried out with the support shaft having a lumen, the flexible portion being contained within the lumen when the loop is in the collapsed position. The introducing step can be carried out with the flexible portion having a radius of curvature when in the folded position of less than 0.012 inch. The introducing step can be carried out with the flexible portion being at least twice as flexible in bending as the first end and the second end of the elongate element when the loop is in the expanded position, the flexible portion having a maximum outer dimension of no more than 0.003 inch. The positioning step can be carried out with the elongate element having a first half extending from the first end to a midpoint to define a first length and a second half extending from the second end to the midpoint to define a second length when the loop is in the expanded position, the elongate having a total length in the expanded position. The positioning step can be carried out with an intermediate loop being formed when half of the total length has been deployed, the intermediate loop being positioned distal to a distal end of the support shaft.

The introducing step can be carried out with the first and second ends of the elongate element both being movable relative to the support shaft to move the loop from the collapsed position to the expanded position, the first end having an elbow extending from the support shaft when the loop is in the expanded position; and the positioning step can be carried out so that the elbow is not yet deployed in the intermediate position. The positioning step can be carried out with the elbow partially deployed and moved between the lens and the capsular bag. The positioning step can be carried out by moving the elbow while the elbow is in contact with the lens so that the lens deflects a tip of the elbow toward the support shaft. The positioning step can be carried out with the elbow being moved so that an angle between the support shaft and the elbow is reduced by at least 30 degrees. The positioning step can be carried out with the elbow being moved by rotating the support shaft. The positioning step can be carried out with the elbow moving to a position between the support shaft and the lens when the elbow is moved. The positioning step can be carried out by advancing the second end between the capsular bag and the lens in a distal direction to an opposing edge position in the intermediate position, the opposing edge position is a position which is at least 90% of a radius of the lens and within 60 degrees of an opposing edge, the opposing edge is defined as a projection of a longitudinal axis of the support shaft to a circumference of the lens when viewed along an axis of the lens.

The introducing step can be carried out with the first end and the second end being advanced simultaneously. The introducing step can be carried out with the elongate element having an unshaped portion and a pre-shaped portion when the loop is in the expanded position, the second end of the elongate element being movable relative to the support shaft to change the size of the loop, the elongate element having a first half extending from the first end to a midpoint and a second half extending from the second end to the midpoint when the loop is in the open position, the elongate element having a total length defined by the exposed length of the elongate element when the loop is in the expanded position. The introducing step can be carried out with the shaped portion being 40%-75% of a total length of the elongate element. The introducing step can be carried out with the unshaped portion being 25%-60% of the total length. The introducing step can be carried out with the shaped portion being at least 50% and the unshaped portion being at least 25% of the total length. The introducing step can be carried out with at least 80% of the unshaped portion being along the second half. The introducing step can be carried out with at least 80% of the shaped portion being along the first half. The introducing step can be carried out with the unshaped portion being no more than 25% deployed when half of the total length of the elongate element has been deployed. The introducing step can be carried out with the first end also being movable relative to the support shaft to move the shaft between the collapsed and expanded positions. The introducing step can be carried out with at least 80% of the shaped portion being along the second half. The introducing step can be carried out with the first end attached to the support shaft, the first end having an elbow extending proximally from the support shaft when the loop is in the expanded position. The introducing step can be carried out with the support shaft being part of a fluid handling device, the fluid handling device having a first fluid lumen. The positioning step can be carried out with the elongate element extending from the fluid handling device into a space between the lens and the capsular bag.

The method further includes withdrawing the elongate element into the fluid handling device after the cutting step so that the elongate element is not positioned within the first fluid lumen of the fluid handling device and without removing the fluid handling device from the eye. The introducing step can be carried out with the fluid handling device having a second fluid lumen. The introducing step can be carried out with the support shaft having a first tube and a second tube, the first tube having the first fluid lumen and the second tube having the second fluid lumen. The introducing step can be carried out with the first tube extending through the second fluid lumen. The introducing step can be carried out with the first end being coupled to the first tube and the second end being longitudinally movable relative to the support shaft to move the loop between the collapsed and expanded positions. The introducing step can be carried out with the first end and the second end being movable relative to the support shaft to move the loop between the collapsed and expanded positions. The introducing step can be carried out with the first end extending through the first lumen and the second end extending through the second lumen. The introducing step can be carried out with the first end of the elongate element being attached to the second tube. The introducing step can be carried out with the second end extending through a space between the first tube and the second tube, the second end being movable in the space to change a size of the loop.

The method can further include irrigating the eye with one of the first fluid lumen and the second fluid lumen; and aspirating the eye with the other of the first fluid lumen and the second fluid lumen. The method can further include irrigating the eye with the first fluid lumen in the fluid handling device. The method can further include aspirating the eye with the first fluid lumen. The method can further include releasing one end of the first end and the second end of the elongate element after the cutting step; and withdrawing the one end through the fluid handling device. The method can further include withdrawing the elongate element from the first lumen so that the first lumen is not obstructed by the elongate element after the cutting step. The withdrawing step can be carried out without removing the support shaft from the eye.

The positioning step can be carried out with the support shaft including a first tube having an angled tip, the angled tip having a proximal portion and a distal portion which extends distally and terminates at a distal end of the angled tip, the proximal portion having a proximal orientation and the distal portion having a distal orientation defined by a proximal axis and a distal axis, respectively, of a first lumen in the first tube, the proximal and distal orientations lying in and defining a working plane, the loop generally defining a loop plane which is determined by an orientation that maximizes an area bounded by the loop in the expanded position. The positioning step can be carried out with the working plane oriented less than 45 degrees from the loop plane when the loop is in the expanded position and the loop plane is parallel to the midplane of the lens. The positioning step can be carried out with the working plane oriented less than 20 degrees from the loop plane when the loop is in the expanded position and the loop plane is parallel to the midplane of the lens. The positioning step can be carried out with the distal end of the angled tip being directed away from the loop when the loop is in the expanded position around the lens and the loop plane is perpendicular to the midplane. The positioning step can be carried out with the distal end of the angled tip pointing away from the lens and sweeping an angle of at least 45 degrees when the loop is moved into position around the lens prior to the cutting step. The introducing step can be carried out with the support shaft being a tip of a phacoemulsification device, the phacoemulsification device having a housing with the tip extending from the housing to a distal end, the tip being coupled to a vibrating element mounted to the housing for vibrating the tip, a first lumen extends through the tip and has an opening at the distal end.

The method can further include vibrating the cutting element with the vibrating element to breaking the lens into pieces with the tip. The method can further include removing fluid and lens fragments using the first lumen. The positioning step can be carried out with the elongate element extending from the tip of the phacoemulsification device. The positioning step can be carried out with by moving the elongate element outwardly from the first lumen in the tip. The introducing step can be carried out with the tip including a first tube which extends to the distal end and has the first lumen, the tip also including a second tube positioned around the first tube, the second tube having a second lumen; and the positioning step can be carried out with by moving the elongate element outwardly to extend from the tip. The introducing step can be carried out with the second tube being a polymer sheath and the first tube being a metal tube.

The method can further include removing the elongate element from the eye without withdrawing the distal end of the tip from the eye. The method can further include coupling a controller to the elongate element, the controller being operable to change a size of the loop. The coupling step can be carried out with the controller and the elongate element being initially separated, the elongate element being the coupled to an introducer which is advanced distally through the first lumen until the introducer extends from an opening in the lumen at a distal end of the tip, the elongate element being coupled to the introducer when the actuator extends from the distal end of the lumen, the elongate element being introduced into the lumen in a proximal direction through the distal end of the lumen by moving the introducer proximally into the lumen. The cutting step can be carried out with the elongate element having a stop at the first end, the stop being in contact with the first tube during the cutting step to stabilize the first end of the elongate element. The method can further include withdrawing the elongate element into the first lumen after the cutting step, the stop decreasing in a dimension which decreases contact with the first tube when the elongate element is withdrawn into the first lumen. The withdrawing step can be carried out by removing the elongate element completely from the first lumen. The method can further include aspirating lens fragments through the first lumen after the withdrawing step.

The positioning step can be carried out with the first end of the elongate element being coupled to the second tube. The positioning step can be carried out with the first end and the second end both being coupled to the second tube. The introducing step can be carried out with the second tube of the support shaft having an opening in the second lumen; the positioning step can be carried out with the first end of the elongate element extending through the opening in the second lumen. The introducing step can be carried out with the first tube extending through the second lumen in the second tube. The removing step can be carried out by withdrawing the elongate element through the second lumen. The introducing step can be carried out with the second lumen forming by a space between the first tube and the second tube; and the removing step being carried out by withdrawing the elongate element through the space.

The method can further include delivering a fluid to the eye through the space. The positioning step can be carried out with the support shaft including a first tube having an angled tip, the angled tip having a proximal portion and a distal portion which extends distally and terminates at a distal end of the angled tip, the proximal portion having a proximal orientation and the distal portion having a distal orientation defined by a proximal axis and a distal axis, respectively, of a first lumen in the first tube, the proximal and distal orientations lying in and defining a working plane, the loop generally defining a loop plane which is determined by an orientation that maximizes an area bounded by the loop in the expanded position. The positioning step can be carried out with the working plane oriented less than 45 degrees from the loop plane when the loop is in the expanded position and the loop plane is parallel to the midplane of the lens. The positioning step can be carried out with the working plane oriented less than 20 degrees from the loop plane when the loop is in the expanded position and the loop plane is parallel to the midplane of the lens. The positioning step can be carried out with the distal end of the angled tip being directed away from the loop when the loop is in the expanded position around the lens and the loop plane is perpendicular to the midplane. The positioning step can be carried out with the distal end of the angled tip pointing away from the lens and sweeping an angle of at least 45 degrees when the loop is moved into position around the lens prior to the cutting step. The positioning step can be carried out with the first end of the elongate element being a fixed end and the second end being a movable end. The positioning step can be carried out with the elongate element expanding into the space between the capsular bag and the anterior side of the lens due to natural expansion of the elongate element toward the expanded shape.

The method can further include moving the elongate element between a posterior surface of the lens and the capsular bag to dissect the lens from the capsular bag before the cutting step. The cutting step can be carried out with the lens being whole prior to the cutting step, the cutting step being carried out with the loop extending around a posterior surface and an anterior surface when cutting the lens. The positioning step can be carried out by advancing the second end between the capsular bag and the lens before advancing the first end between the capsular bag and lens. The cutting step can be carried out with the loop positioned around the posterior surface and the anterior surface. The positioning step can be carried out with the elongate element forming the loop together with the support shaft. The introducing step can be carried out with the support shaft being a tip of a phacoemulsification hand piece, the hand piece having a vibrating element coupled to the tip to vibrate the tip. The positioning step can be carried out with the support shaft having an enlarged portion when measured transverse to the longitudinal axis of the support shaft. The introducing step can be carried out with the first end of the elongate element attached to the support shaft, the enlarged portion of the support shaft being formed by a portion of the support shaft to which the elongate element is attached. The method can further include reducing the size of the enlarged portion of the support shaft, the enlarged portion being movable to a reduced size to reduce engagement between the support shaft and the lumen. The reducing step can be carried out with the enlarged portion of the support shaft movable to the reduced size when the elongate element is withdrawn into the lumen, the elongate element displacing a portion of the enlarged portion radially inward and away from the wall of the lumen. The introducing step can be carried out with a fluid Y-arm having a main lumen which splits into a first leg and a second leg, the y-arm being coupled to a connector for the lumen which extends through the tip. The introducing step can be carried out with a controller having an actuator coupled to the elongate element to move the elongate element between the collapsed position and the expanded position. The introducing step can be carried out with the hand piece having a handle. The positioning step can be carried out with the controller attached to a tube which extends proximally from the handle of the hand piece, the controller being positioned proximal to the handle when attached to the tube. The positioning step can be carried out with the controller having a clip which attaches the controller to the tube.

In an interrelated aspect, described is a device for cutting a lens in a cataract procedure. The device includes a support shaft; and an elongate element coupled to the support shaft. The elongate element has a first end and a second end. At least one of the first end and the second end are movable relative to the other end to change a size of a loop formed at least in part by the elongate element. The loop is movable from a collapsed position to an expanded position. The loop is in the collapsed position during the introduced into the eye and is in the expanded position when the loop is positioned around the lens. The lens is cut by reducing a size of the loop when the loop is positioned around the lens.

The elongate element can extend from the first end to the second end when in the expanded position, the first end and the second end being exposed in the expanded position. The second end of the elongate element can be releasably coupled to the support shaft, wherein release of the second end permits withdrawal of the second end from the eye. The elongate element can have an elbow at the first end, the elbow extending from the support shaft when the loop is in the expanded position. The elbow of the elongate element can extend proximally from the support shaft when the loop is in the expanded position. The elongate element can form the loop so that a loop plane is defined in the expanded position, the elbow being at least twice as flexible in bending for a force applied to a tip of the elbow and lying in the loop plane compared to a transverse force applied to the tip of the elbow and directed transverse to the loop plane. The elongate element can be formed with the elbow formed by the elongate element has a living hinge. The elongate element can include living hinge being a crimped portion. The elongate element can be formed with the elbow being integrally formed with the support shaft. The elongate element can be formed with the elbow being made of a polymer. The elongate element can be formed with the elbow being spaced apart from the support shaft, wherein the elbow may be deflected toward the support shaft by rotating the support shaft and engaging the lens when rotating. The elongate element can be formed with the elbow having an unbiased position relative to the support shaft when the loop is in the expanded position, the elbow having a tip having an orientation at the tip which is 90-180 degrees from a distal orientation of the support shaft when the loop is in the expanded position, the distal orientation being a direction of a longitudinal axis of the support shaft at a distal end of the support shaft. The elongate element can be formed with the first end of the elongate element having an elbow, the elbow having an unbiased shape which directs the elbow proximally relative to the support shaft when the loop is in the expanded position. The elongate element can be folded at a flexible portion when the loop is in the collapsed position. The flexible portion can be folded in a U-shape with a first side of the U-shape extending to the first end and a second side of the U-shape extending to the second end. The support shaft can have a lumen, the flexible portion being contained within the lumen when the loop is in the collapsed position. The flexible portion of the elongate element can have a radius of curvature when in the folded position of less than 0.012 inch.

The flexible portion of the elongate element can be at least twice as flexible in bending as the first end and the second end of the elongate element when the loop is in the expanded position. The flexible portion can have a maximum outer dimension of no more than 0.003 inch in cross-section to a longitudinal axis. The elongate element can have a first half extending from the first end to a midpoint to define a first length and a second half extending from the second end to the midpoint to define a second length when the loop is in the expanded position, the elongate having a total length in the expanded position. The elongate element can form an intermediate loop when half of the total length has been deployed, the intermediate loop being positioned distal to a distal end of the support shaft. The elongate element can be formed with the first end and the second end of the elongate element both being movable relative to the support shaft to move the loop from the collapsed position to the expanded position, the first end having an elbow extending from the support shaft when the loop is in the expanded position, the elbow being not deployed in the intermediate position. The elbow of the elongate element can be flexible so that the elbow may be moved in contact with the lens so that the lens deflects a tip of the elbow. The elbow of the elongate element can be movable so that an angle between the support shaft and the elbow is reduced by at least 30 degrees. The second end can be movable relative to the support shaft, the second end being moved to increase a size of the loop so that the elongate element advances between the capsular bag and the lens in a distal direction toward an opposing edge position in the intermediate position, the opposing edge position is a position which is at least 90% of a radius of the lens and within 60 degrees of an opposing edge, the opposing edge is defined as a projection of a longitudinal axis of the support shaft to a circumference of the lens when viewed along an axis of the lens. The elongate element can be manipulatable with the first end and the second end being advanced simultaneously.

The elongate element can have an unshaped portion and a pre-shaped portion when the loop is in the expanded position, the second end of the elongate element being movable relative to the support shaft to change the size of the loop, the elongate element having a first half extending from the first end to a midpoint and a second half extending from the second end to the midpoint when the loop is in the expanded position, the elongate element having a total length defined by an exposed length of the elongate element when the loop is in the expanded position. The shaped portion of the elongate element can be 40%-75% of a total length of the elongate element. The unshaped portion of the elongate element can be 25%-60% of the total length. The shaped portion of the elongate element can be at least 50% and the unshaped portion being at least 25% of the total length. The elongate element can be formed so that at least 80% of the unshaped portion is along the second half of the elongate element. The elongate element can be formed so that at least 80% of the shaped portion is along the first half. The elongate element can be formed with the unshaped portion being no more than 25% deployed when half of the total length of the elongate element has been deployed. The first end of the elongate element can be movable relative to the support shaft to move the loop between the collapsed position and the expanded position. The elongate element can be formed with at least 80% of the shaped portion being along the second half. The first end of the elongate element can be attached to the support shaft, the first end having an elbow extending proximally from the support shaft when the loop is in the expanded position.

The support shaft can be part of a fluid handling device, the fluid handling device having a first fluid lumen. The elongate element can be extendable from the fluid handling device into a space between the lens and the capsular bag. The elongate element can be movable relative to the fluid handling device, the elongate element being movable withdraw the elongate element into fluid handling device without removing the fluid handling device from the eye. The fluid handling device can have a second fluid lumen. The support shaft can have a first tube and a second tube, the first tube having the first fluid lumen and the second tube having the second fluid lumen. The first tube can extend through the second fluid lumen. The first end of the elongate element can be coupled to the first tube and the second end being longitudinally movable relative to the support shaft to move the loop between the collapsed position and the expanded position. The first end and the second end can be movable relative to the support shaft to move the loop between the collapsed position and the expanded position. The first end of the elongate element can extend through the first lumen and the second end extends through the second lumen. The first end of the elongate element can be attached to the second tube. The second end of the elongate element can extend through a space between the first tube and the second tube, the second end being movable in the space to change a size of the loop. One of the first fluid lumen and the second fluid lumen can be coupled to a source of fluid and the other of the first and second lumens is coupled to a suction source. At least one of the first end and the second end can be movable to withdraw the at least one of the first end and the second end into the fluid handling device. The elongate element can be movable and positioned within the first lumen, the elongate element being removable from the first lumen so that the first lumen is not obstructed by the elongate element. The elongate element can be movable within the first lumen to withdraw the elongate element into the fluid handling device without removing the fluid handling device from the eye.

The support shaft can include a first tube having an angled tip, the angled tip having a proximal portion and a distal portion which extends distally and terminates at a distal end of the angled tip, the proximal portion having a proximal orientation and the distal portion having a distal orientation defined by a proximal axis and a distal axis, respectively, of a first lumen in the first tube, the proximal orientation and the distal orientation lying in and defining a working plane, the loop generally defining a loop plane which is defined by an orientation that maximizes an area bounded by the loop in the expanded position.

The angled tip can be formed with the working plane oriented less than 45 degrees from the loop plane when the loop is in the expanded position and the loop plane is parallel to the midplane of the lens. The angled tip can be formed with the working plane oriented less than 20 degrees from the loop plane when the loop is in the expanded position and the loop plane is parallel to the midplane of the lens. The angled tip can be formed so that the distal end of the angled tip is directed away from the loop when the loop is in the expanded position around the lens and the loop plane is perpendicular to the midplane. The angled tip can be formed so that the distal end of the angled tip points away from the lens and sweeps an angle of at least 45 degrees when the loop is moved into position around the lens prior to the cutting the lens.

The device can further include a phacoemulsification device with the support shaft being a tip of the phacoemulsification device, the phacoemulsification device having a housing with the tip extending from the housing to a distal end, the tip being coupled to a vibrating element mounted to the housing for vibrating the tip, a first lumen extends through the tip and has an opening at the distal end of the tip. The tip can be coupled to the vibrating element so that the tip may be vibrated when breaking the lens into pieces with the tip. The first lumen can be coupled to a source of suction for removing fluid and lens fragments through the first lumen. The elongate element can extend from the tip of the phacoemulsification device when the loop moves toward the expanded position. The elongate element can be movable outwardly from the first lumen in the tip when the loop moves from the collapsed position to the expanded position. The tip can include a first tube which extends to the distal end, the first tube having the first lumen, the tip also including a second tube positioned around the first tube, the second tube having a second lumen, the elongate element being movable outwardly to extend from the tip. The second tube can be a polymer sheath and the first tube is a metal tube. The elongate element can be movable to withdraw the elongate element from the eye without withdrawing the distal end of the tip from the eye.

The device can further include a controller coupled to the elongate element, the controller being operable to change a size of the loop. The controller and the elongate element can be initially separated, the elongate element being coupled to an introducer which is advanced distally through the first lumen until the introducer extends from an opening in the lumen at a distal end of the tip, the elongate element being configured to be coupled to the introducer when the actuator extends from the distal end of the lumen, the elongate element being introduced into the first lumen in a proximal direction through the distal end of the first lumen by moving the introducer proximally into the first lumen. The elongate element can have a stop at the first end, the stop being in contact with the first tube during cutting to stabilize the first end of the elongate element. The elongate element can be movable within the first lumen, the elongate element being movable within the first lumen to withdraw the elongate element into the first lumen, wherein withdrawing the elongate element decreases a dimension in the stop which decreases contact with the first tube when the elongate element is withdrawn. The elongate element can be movable to completely remove the elongate element from the first lumen. The first lumen can be coupled to a suction source to aspirate lens fragments through the first lumen. The first end of the elongate element can be coupled to the second tube. The first end and the second end of the elongate element both can be coupled to the second tube.

The second tube of the support shaft can have an opening in the second lumen; the first end of the elongate element extends through the opening in the second lumen when the loop is in the expanded position. The first tube can extend through the second lumen in the second tube. The elongate element can be movable to withdraw the elongate element through the second lumen. The second lumen can form a space between the first tube and the second tube; and the elongate element extending through the space and being removable from the eye by withdrawing the elongate element into the space. The second lumen of the second tube can be coupled to a fluid supply to deliver the fluid to the eye through the second lumen.

The support shaft can include a first tube having an angled tip, the angled tip having a proximal portion and a distal portion which extends distally and terminates at a distal end of the angled tip, the proximal portion having a proximal orientation and the distal portion having a distal orientation defined by a proximal axis and a distal axis, respectively, of a first lumen in the first tube, the proximal orientation and the distal orientation lying in and defining a working plane, the loop generally defines a loop plane which is determined by an orientation that maximizes an area bounded by the loop in the expanded position.

The working plane formed by the proximal and distal orientations of the angled tip can be oriented less than 45 degrees from the loop plane when the loop is in the expanded position and the loop plane is parallel to the midplane of the lens. The working plane formed by the proximal and distal orientations of the angled tip can be oriented less than 20 degrees from the loop plane when the loop is in the expanded position and the loop plane is parallel to the midplane of the lens. The distal end of the angled tip can be directed away from the loop when the loop is in the expanded position. The distal end of the angled tip can point away from the lens when the loop is moved into position around the lens prior to cutting the lens. The first end of the elongate element can be a fixed end and the second end being a movable end. The elongate element can expand into a space between the capsular bag and the anterior side of the lens due to natural expansion of the elongate element toward the expanded shape. The loop can be sized and configured to be positioned around a posterior surface and an anterior surface of the lens and the lens being whole prior to cutting the lens. The second end of the elongate element can be advanced between the capsular bag and the lens before advancing the first end between the capsular bag and lens when the loop is in an intermediate position. The elongate element can form the loop together with the support shaft.

The support shaft can be a tip of a phacoemulsification hand piece, the hand piece having a vibrating element coupled to the tip to vibrate the tip.

The support shaft can have an enlarged portion when measured transverse to the longitudinal axis of the support shaft. The first end of the elongate element can be attached to the support shaft; the enlarged portion of the support shaft being formed by a portion of the support shaft to which the elongate element is attached. The enlarged portion of the support shaft can be movable to a reduced size to reduce engagement between the support shaft and the fluid lumen. The enlarged portion of the support shaft can be movable to the reduced size when the elongate element is withdrawn into the lumen of the support shaft, the elongate element displacing a portion of the enlarged portion radially inward and away from the wall of the lumen.

The device can have a fluid Y-arm having a main lumen which splits into a first leg and a second leg, the main lumen being coupled to a lumen in the hand piece. The device can have a controller having an actuator coupled to the elongate element to move the elongate element between the collapsed position and the expanded position. The device can have a handle; and the controller can be attached to a tube extending proximally from the handle, the controller being positioned proximal to the handle when attached to the tube. The controller can include a clip that attaches the controller to the tube. The device can further include a fluid y-arm having a main lumen and a first leg and a second leg. The device can further include a controller attached to one of the first and second legs, the controller having an actuator coupled to the elongate element to manipulate the elongate element.

The device can further include a source of irrigation fluid. The source of irrigation fluid can be fluidly coupled to a lumen in the support shaft. The source of irrigation fluid can be fluidly coupled to a first tube, the first tube configured to be positioned over a phacoemulsification tip for delivering the irrigation fluid. The elongate element can include a flexible portion, the flexible portion having a folded lateral dimension which is no more than 2.5 times the outer dimension of the flexible portion when in the folded position. The angled tip can be oriented with an offset angle of 90 to 180 degrees relative to the loop plane, the offset angle is the angle which the tip is rotated from an origin position in which the loop plane is parallel to the working plane and the tip directed at the loop in the origin position.

BRIEF DESCRIPTION OF THE DRAWINGS

These and other aspects will now be described in detail with reference to the following drawings. Generally speaking the figures are not to scale in absolute terms or comparatively, but are intended to be illustrative. Also, relative placement of features and elements may be modified for the purpose of illustrative clarity.

FIG. 16A shows a two-lumen design with the loop to expanding away from the angled tip;

FIG. 16B shows a side view of the loop of FIG. 16A;

FIG. 16C shows a coaxial design with the elongate element extending through the space between the first and second tubes;

FIG. 28 shows the controller;

FIG. 29 shows an end view of the controller;

FIG. 30 shows a side view of the controller;

Figure 1:
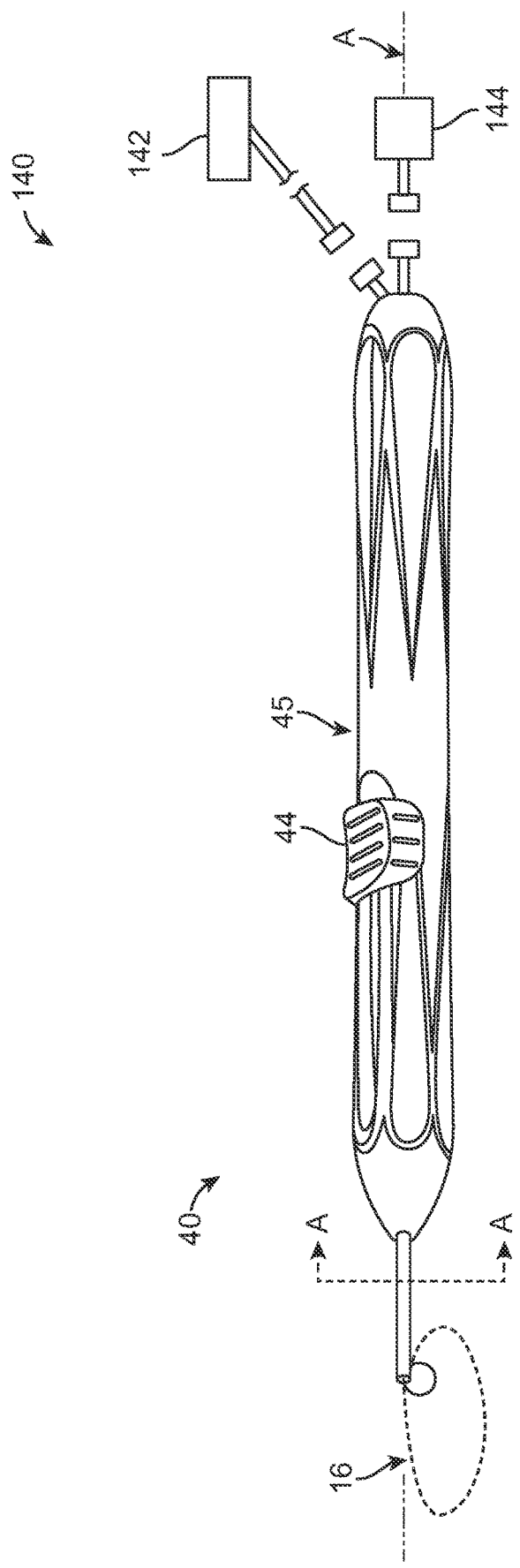
FIG. 1 shows a device for cutting a lens in an eye with irrigation and aspiration lumens.

It should be appreciated that the drawings are for example only and are not meant to be to scale. It is to be understood that devices described herein may include features not necessarily depicted in each figure.

DETAILED DESCRIPTION

Described herein are methods and devices for cutting a lens in a cataract procedure. The devices described herein can have an elongate element coupled to a support shaft that may have first lumen. The elongate element has a first end and a second end with at least one of the first and second ends being movable relative to the other to change a size of a loop. The loop is formed at least in part by the elongate element and may also be formed in part by the support shaft. The loop is movable from a collapsed position to an expanded position with the loop in the collapsed position during introduction. The loop may be fully contained within the device, such as within the first lumen, in the collapsed position or may form a small loop which is exposed in the collapsed position.

In use, the loop expands and advances between the capsular bag and the lens when deployed. The loop is advanced and expanded until the loop reaches the expanded position. The loop is then moved to the posterior side of the lens by rotating the shaft. The loop may be used to separate the posterior surface of the lens and the capsular bag by sweeping the loop through this area. The loop is then positioned around the lens at the desired position to form the first cut. The loop is then reduced in size to cut the lens.

The elongate element may have an elbow at the first end. The elbow may extend proximally from the support shaft when the loop is expanded. The elbow may be at least twice as flexible in bending for a force applied to a tip of the elbow in a loop plane compared to a transverse force applied to the tip (the transverse force being applied in a direction transverse to the loop plane). The loop generally defines a loop plane in the expanded position which is defined by an orientation that maximizes the area of the loop. The elbow may have a hinge, such as a living hinge, to provide the requisite flexibility. The living hinge may be formed by crimping the elbow or in any other suitable manner such as a non-circular cross-section having the desired properties. The elbow may be made of a polymer and attached to the support shaft or may be integrally formed with the support shaft as shown.

In one aspect, the elbow may be positioned between the support shaft and the lens by rotating the shaft to deflect the elbow toward the support shaft when initially expanding the loop. The tip of the elbow has an orientation which is 90-180 degrees from a distal orientation of the support shaft when the loop is expanded.

The elongate element may also have a flexible portion which permits the elongate element to be folded and contained within the first lumen when the loop is collapsed. The flexible portion is folded in a U-shape with a first side extending toward the first end and a second side extending toward the second end. The flexible portion may have a radius of curvature when folded in the lumen of less than 0.012 inch. The flexible portion may also be at least twice as flexible in bending as the first and second ends of the elongate element. The flexible portion may have a maximum outer dimension of no more than 0.003 inch measured transverse to the longitudinal axis of the elongate element. The flexible portion may be a monofilament or any other suitable material.

The elongate element has a first half extending from the midpoint toward the first end (which defines a first length of the elongate element) and a second half extending from the midpoint toward the second end (which defines a second length of the elongate element) when the loop is expanded. The loop forms an intermediate loop and is in an intermediate position when half of the total length has been deployed. "Deployed" as used for this purpose shall mean the exposed part of the elongate element.

The intermediate loop may be positioned distal to a distal end of the support shaft so that the loop is deployed distally from the support shaft. When using the elbow, the elbow may be deployed rather than attached to the support shaft. For example, the elbow may remain within the lumen in the intermediate position when the first and second ends are advanced simultaneously (or independently). The loop may be partially deployed and the elbow moved or tucked between the lens and the capsular bag as described below.

The first end of the elongate element may be movable relative to the support shaft to move the shaft between the collapsed and expanded positions. The first end may be attached to the support shaft with the first end having the elbow extending proximally from the support shaft when the loop is expanded. The elbow may also be deflected by the lens by placing the elbow in contact with the lens and rotating the support shaft. The lens deflects the tip of the elbow toward the support shaft so that an angle between the support shaft and the elbow is reduced by at least 30 degrees.

The loop may be deployed by advancing the second end between the capsular bag and the lens in a distal direction to an opposing edge position when the loop is in the intermediate position. The opposing edge position is at least 90% of a radius of the lens and within 60 degrees of an opposing edge defined as a projection of the longitudinal axis of the support shaft to the lens circumference when viewed along the central axis of the lens. Deploying the loop in this manner establishes the distal aspect of the loop first followed by proximal expansion of the loop.

The elongate element may have both a pre-shaped portion and an unshaped portion when the loop is in the expanded position. The shaped portion may be 40%-75% of the total length of the elongate element while the unshaped portion may be 25%-60% of the total length. In another aspect, the shaped portion is at least 50% of the total length and the unshaped portion is at least 25% of the total length. In still another aspect, at least 80% of the unshaped portion is along either the first half or second half. In yet another aspect, the unshaped portion may be no more than 25% deployed when half of the total length has been deployed (intermediate position). One of the ends, such as the first end, may be released after cutting the lens and the elongate element withdrawn into the device.

In a specific aspect, the device may be coupled to a fluid handling device which may be an irrigation and/or aspiration device or a phacoemulsification device. The phacoemulsification device breaks the lens fragments formed by the loop into smaller pieces which are aspirated through a lumen in the phacoemulsification device in the conventional manner. The cutting device may also be used with an irrigation and/or aspiration device.

An advantage of the devices and methods described herein is that removal of the lens cutting device and introduction and exchange of the other device is not necessary. This avoids possible issues with fluid loss and exchange of devices since the tip of the device remains in the eye. For example, the support shaft may have a first lumen for irrigation or aspiration. The elongate element may be positioned in the first lumen for deploying and manipulating the loop. The elongate element may be withdrawn into the device after cutting the lens so that the elongate element is not positioned in the first lumen for unimpeded flow through the first lumen. The elongate element is also withdrawn without removing the tip of the fluid handling device from the eye.

For a device with aspiration and irrigation, the support shaft may have a first tube and a second tube with the first tube having the first lumen and the second tube having a second lumen. The first tube also may extend through the second fluid lumen or may be independent (such as side-by-side).

The first end of the elongate element may be coupled to the first tube while the second end is movable relative to the support shaft to move the loop between the collapsed and expanded positions. Alternatively, both the first and second ends may be movable with the first end extending through the first lumen and the second end extending through the second lumen. In still another alternative, the first end of the elongate element may be attached to the second tube while the second end extends through a space between the first and second tubes.

The fluid handling device may be used to irrigate and/or aspirate the eye. To this end, fluid may be irrigated through one of the first and second fluid lumens while the other lumen is used to aspirate fluid and lens fragments. The elongate element may be withdrawn to remove the elongate element from the fluid lumen so that the elongate element does not impede aspiration or irrigation.

The device may also have a support shaft with an angled tip. The angled tip has a proximal portion, with a proximal orientation, and a distal portion with a distal orientation. The proximal and distal orientations lie in, and define, a working plane oriented less than 45 degrees, or less than 20 degrees, from the loop plane when the loop is expanded. Furthermore, the distal end of the angled tip is directed away from the loop when the loop is expanded. Stated another way, the distal end of the angled tip points away from the lens when the loop is moved into position around the lens for cutting. Orienting the tip in this manner relative to the loop may help reduce the chance of damaging the eye with the tip when manipulating the loop.

The devices described herein may also be used with the phacoemulsification device. The phacoemulsification device has a housing with the tip extending from the housing to a distal end. The tip is coupled to a vibrating element which is activated to vibrate the tip and break the lens into smaller pieces. A first lumen extends through the tip and has an opening at the distal end. Fluid and material may be aspirated through the first lumen in the known manner. The support shaft may include a second tube which may be a polymer sheath while a first tube may be a metal tube both being well known in the art of phacoemulsification devices.

The device includes a controller coupled to the elongate element for manipulating the elongate element between the collapsed and expanded positions and to change the size of the loop. The controller and the elongate element are initially separated and the elongate element is coupled to an introducer and backloaded through the distal end of the lumen. The introducer is advanced distally through the first lumen until the introducer extends from the distal end. The elongate element is then coupled to the introducer when the actuator extends from the distal end of the lumen and the elongate element is then backloaded into the lumen through the distal end of the lumen by pulling the introducer proximally until the support shaft is almost completely within the lumen. The term "backload" or "backloaded" as used herein shall refer to loading in a proximal direction with distal defined as toward the working end while proximal refers to toward the handle.

The elongate element also has a stop at the first end which helps stabilize the elongate element (and therefore the loop) when deploying and manipulating the loop and when cutting the lens. The stop is in contact with the first tube during the cutting step to stabilize the elongate element (and therefore the loop). The elongate element may be withdrawn into the first lumen after cutting the lens. When the elongate element is withdrawn into the first lumen, the stop decreases in a dimension (such as transverse to the longitudinal axis of the elongate element) which decreases contact with the first tube so that the stop may be withdrawn through the first lumen.

The loop is used in the same manner as described herein and all such methods are incorporated here. After cutting the lens with the loop and withdrawing the elongate element from the lumen, the phacoemulsification device may be used in the known manner. For example, the tip is vibrated and used to break up the lens fragments with pieces of the lens and fluid aspirated through the first lumen.

The phacoemulsification device may also have an angled tip. The angled tip may be oriented and shaped with the features discussed above in relation to the irrigation and aspiration device with the angled tip. The angled tip may also be oriented relative to the loop as mentioned above in relation to the aspiration and irrigation device(s).

In use, the loop can expand into the space between the capsular bag and the anterior side of the lens due to natural expansion of the elongate element toward the expanded shape. The elongate element may also be moved between the posterior surface of the lens and the capsular bag to dissect the lens from the capsular bag before cutting the lens. The devices described herein may be used to cut the lens when the lens is removed from the capsular bag and is particularly useful in cutting the lens without removing the lens from the capsular bag. Furthermore, the lens may be whole initially with the loop extending around the posterior and anterior surfaces when the lens is cut.

Now with respect to the drawings, FIGS. 1-4 show a device 40 for cutting a lens. The device 40 can include a hand piece 45 and an elongate element 16 coupled to a support shaft 12 extending from a distal end of the hand piece 45. The hand piece 45 can include one or more actuators 44 for actuating the elongate element 16. The device 40 may be used independently or as a part of or in conjunction with a fluid handling device 140 configured to provide irrigation and/or aspiration.

The elongate element 16 can have a first end 17 and a second end 19 with at least one of the first and second ends 17, 19 being movable relative to the other to change a size of a loop 21 formed, at least in part, by the elongate element 16. The loop 21 is movable from a collapsed position (solid line position of FIG. 1) to an expanded position (dotted line position of FIG. 1). The loop 21 is in the collapsed position when introduced into the eye and is in the expanded position when positioned around the lens prior to cutting the lens. The lens is cut by reducing the size of the loop 21 back towards the collapsed position. The loop 21 may be completely contained within the support shaft 12 when introduced into the eye (described below) or may be partially formed and exposed during introduction in the collapsed position shown in the dotted line position of FIG. 1. The loop 21 may be formed entirely by the elongate element 16 or may be formed by the elongate element 16 and the support shaft 12.

Figure 4:
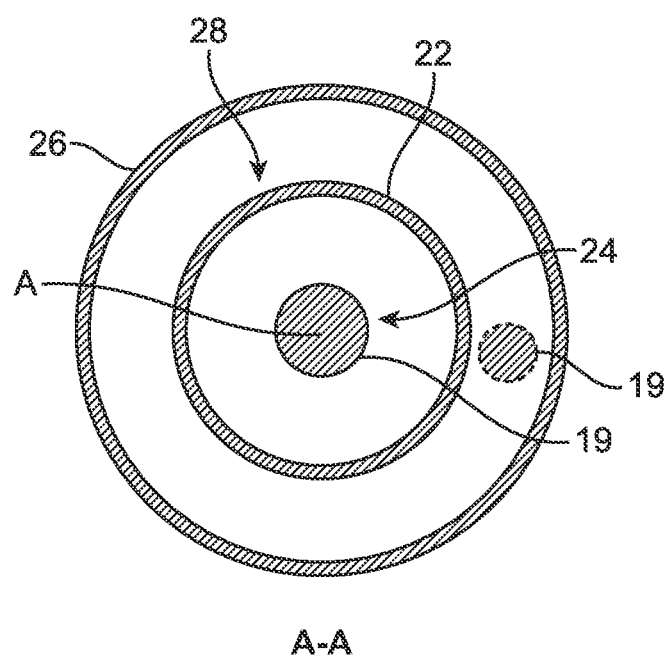
FIG. 4 is a cross-sectional view of FIG. 3 at A-A.

The support shaft 12 can have a first tube 22 having a first lumen 24 and a second tube 26 having a second lumen 28 (see FIG. 4). The second end 19 of the elongate element 16 can extend through a space between the first tube 22 and the second tube 26 in the dotted line position or within the first lumen 24 as shown in the solid line position. The second end 19 of the elongate element 16 can be longitudinally movable to change the size of the loop 21. The first end 17 of the elongate element 16 can be coupled to the first tube 22 and the second end 19 can be longitudinally movable relative to the first and second tubes 22, 24 to move the loop 21 between the collapsed and expanded positions. The device 40 may be used to irrigate and/or aspirate the eye as is known in the art. To this end, the eye may be irrigated with one of the first fluid lumen 24 and the second fluid lumen 28 and aspirated with the other lumen. A source 142 of irrigation can be coupled to the second lumen 28 and a source 144 of suction or vacuum can be coupled to the first lumen 24 (see FIG. 1). The vacuum source 144 and the irrigation source 142 may be any suitable system including computer controlled, user controlled foot pedal actuation, and a conventional gravity fed irrigation bag.

Figure 5:
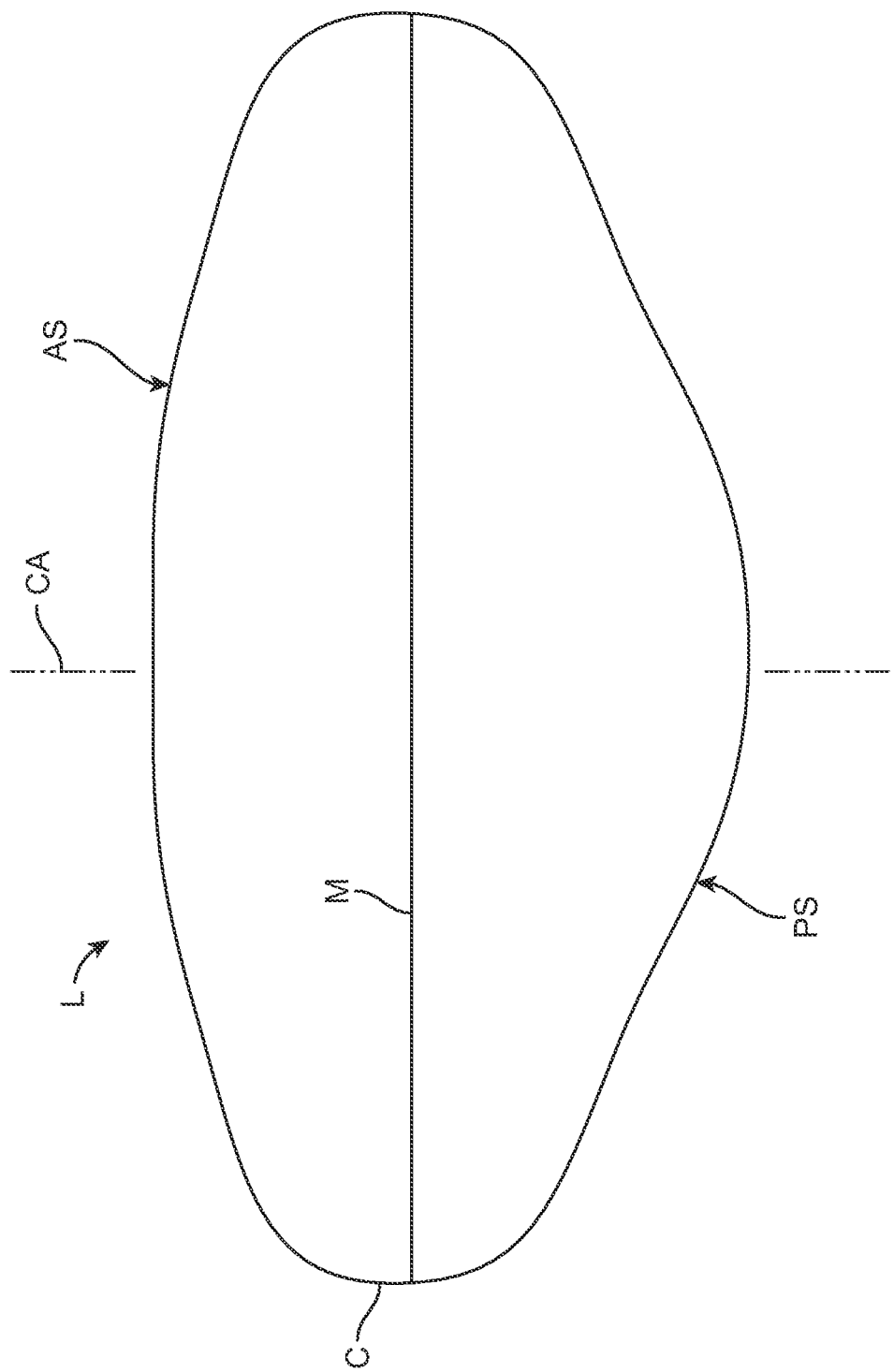
FIG. 5 is a side view of a lens.

FIG. 5 illustrates a schematic of the lens L. The lens L has a central axis CA, a posterior surface PS and an anterior surface AS with an intersection or separation of those surfaces being a circumference C of the lens L. The circumference C lies in and defines a midplane M of the lens L. The lens L resides within a capsular bag (not shown), which separates the posterior vitreous cavity from the anterior chamber (located between the capsular bag and the cornea).

Referring again to FIG. 2, the elongate element 16 may have a pre-shaped portion 32 and an unshaped portion 34 when the loop 21 is in the expanded position. The term "expanded position" as used herein refers to the state of the loop 21 when positioned around the lens L just prior to cutting the lens L. When the loop 21 includes the unshaped portion 34, the loop 21 may take various shapes in the expanded position without departing from the meaning of expanded position or shape. The term "un-shaped" means shapeless or straight like a thin thread or filament such as suture, which has no particular shape in an unbiased (i.e. unconstrained) position. The term "pre-shaped" means any predetermined shape in the unbiased position other than straight unless identified as so explicitly. At times, the term "straight" shall be used in connection with the shaped portion, in that the shaped portion is intended to be a pre-shaped portion. In this instance, when straight is explicitly claimed, the term "shapeless" shall not include "straight" within its meaning.

Use of the unshaped portion 34 may increase the flexibility of the loop 21 during deployment and may help reduce the likelihood of damaging the capsular bag when the loop 21 is initially advanced into position between the capsular bag and lens. The unshaped portion 34 may also help the loop 21 take somewhat different shapes and orientations when deployed to accommodate different angles of approach, geometry, and variations in manipulating the loop 21 by users. The pre-shaped portions 32, on the other hand, can provide sufficient strength and shape to deploy the loop 21 around the lens and to provide a somewhat predetermined expansion of the loop 21. The shaped portion 32 may also help to deploy the loop 21 in a somewhat controlled manner due to natural expansion of the loop 21 rather than rely on buckling or bowing of a cutting member.

Figure 2:
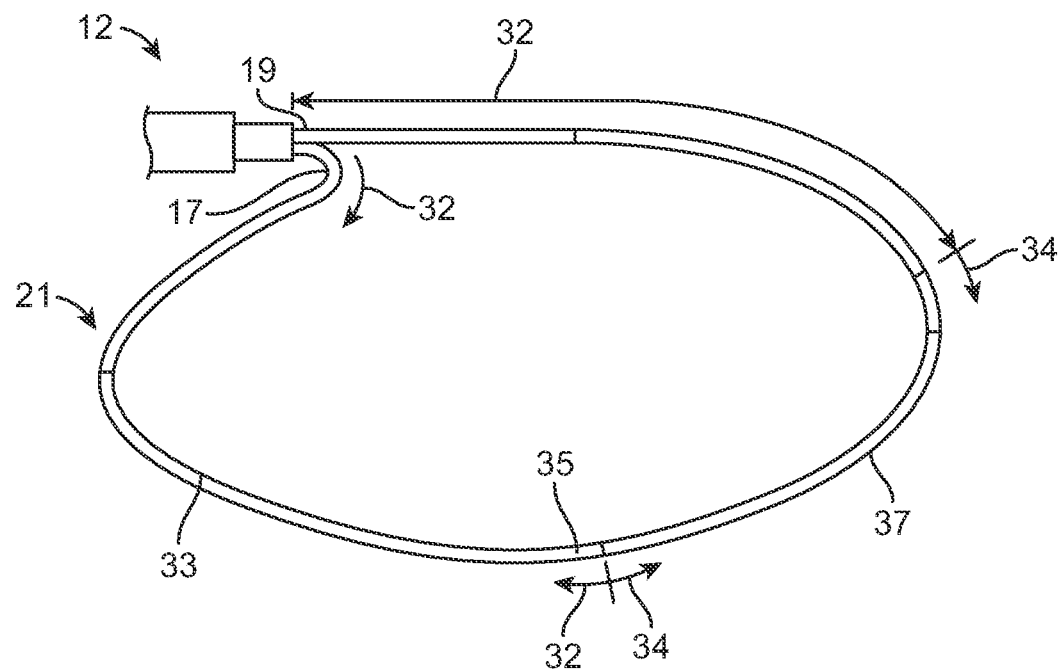
FIG. 2 shows the elongate element of FIG. 1 forming a loop.
Figure 3:
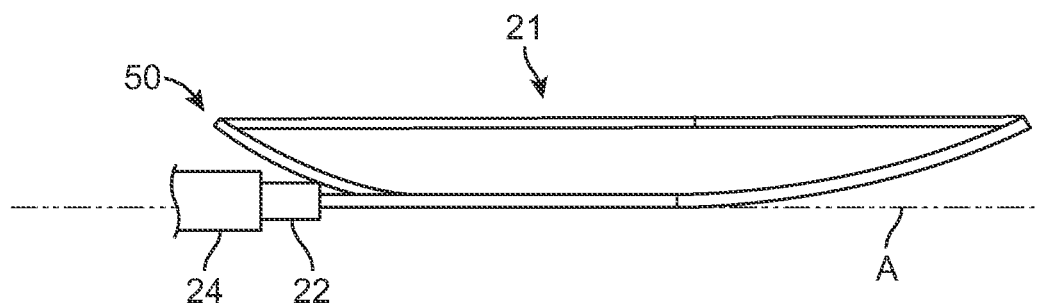
FIG. 3 shows a side view of the loop FIG. 2.

Referring to FIG. 2, the shaped portion 32 may be 40%-75% of a total length and the unshaped portion 34 may be 25%-60% of the total length. Stated another way, the shaped portion 32 may be at least 50% of the total length and the unshaped portion 34 may be at least 25% of the total length. The total length is the length of the elongate element 16 that is deployed or exposed in the expanded position. The elongate element 16 can have a first half 33 that extends from the midpoint 35 toward the first end 17, and a second half 37 that extends from the midpoint 35 toward the second end 19. The shaped portion 32 may be substantially deployed and positioned along the first half 33 so that at least 80% of the pre-shaped portion 32 is along the first half 33 while at least 80% of the unshaped portion 34 is along the second half 37. In another aspect, the unshaped portion 34 may be no more than 10% deployed when half of the total length is deployed. The shaped and unshaped portions 32, 34 may be in one or more segments with the segments being added together when assessing the amount or percentage of the shaped or unshaped portions 32, 34.

In use, the device 40 can be introduced into the eye in a conventional manner. For example, an opening such as a capsulorhexis or any other access opening can be formed in the capsular bag. The loop 21 formed by the elongate element 16 can be tucked between the capsular bag and the lens with the loop 21 in a relatively small size (which may be the collapsed position or expanded somewhat from the collapsed position). The first half 33 of the elongate element 16 that is deployed can be the shaped portion 32 to establish and maintain the proximal end of the loop 21. The unshaped portion 34 can then be deployed and the elongate element 16 may have a shaped portion 32 (a shape including straight) deployed in the final stages to move the unshaped portion 34 to form the distal second half 37 of the loop 21. The straight section 32 shown in FIG. 2 to be somewhat curved may be substantially straight in an unbiased condition.

Figure 6:
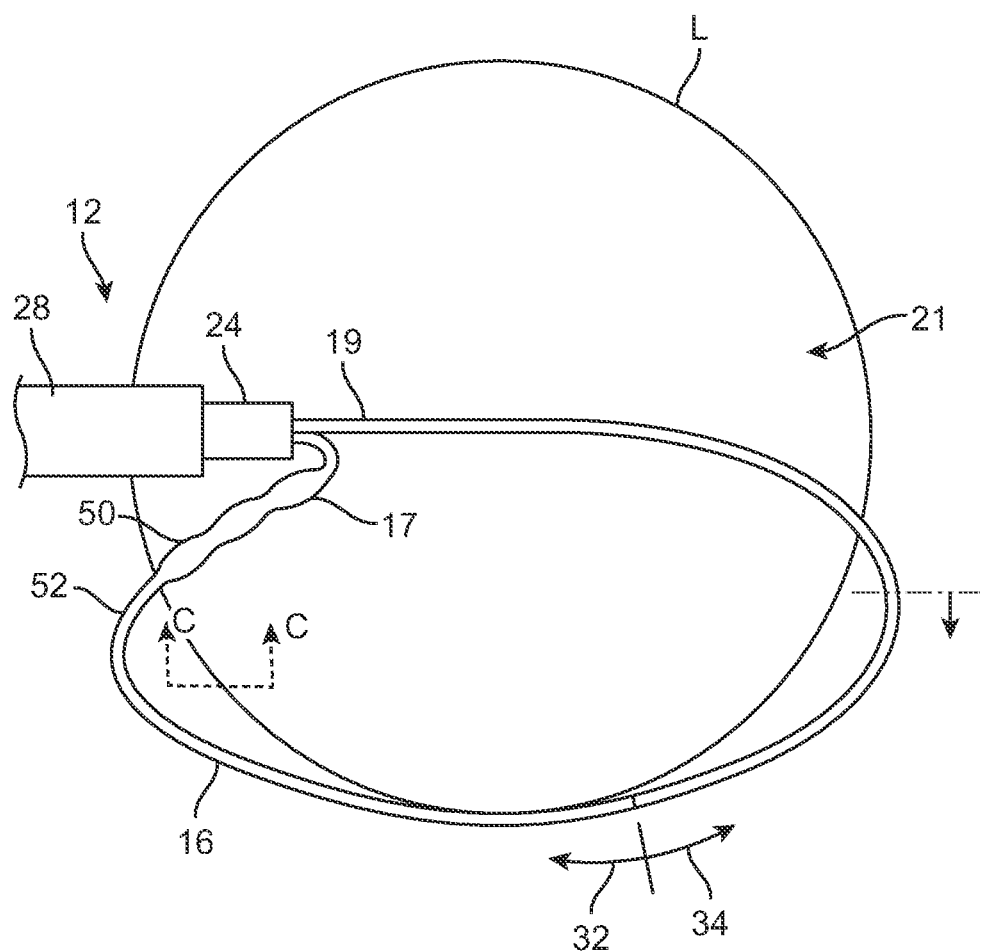
FIG. 6 shows another device for cutting a lens which has an elbow along the elongate element.
Figure 7:
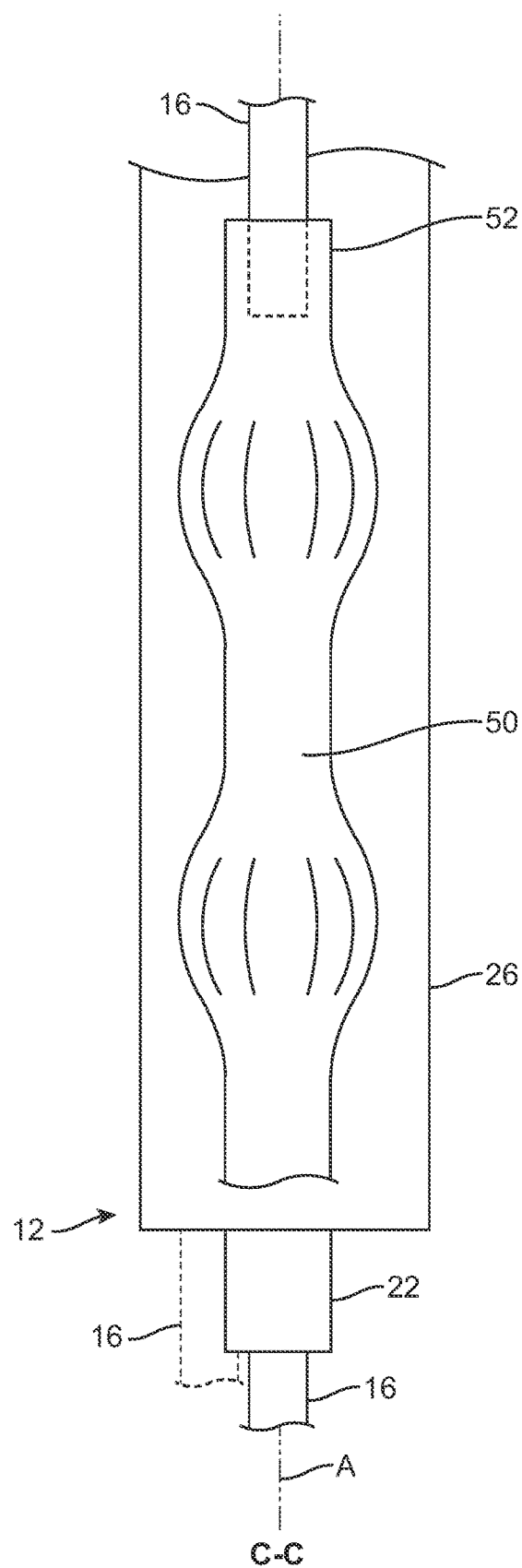
FIG. 7 is a side view of the device of FIG. 6 showing the elbow and the crimped portions of the elbow.
Figure 8:
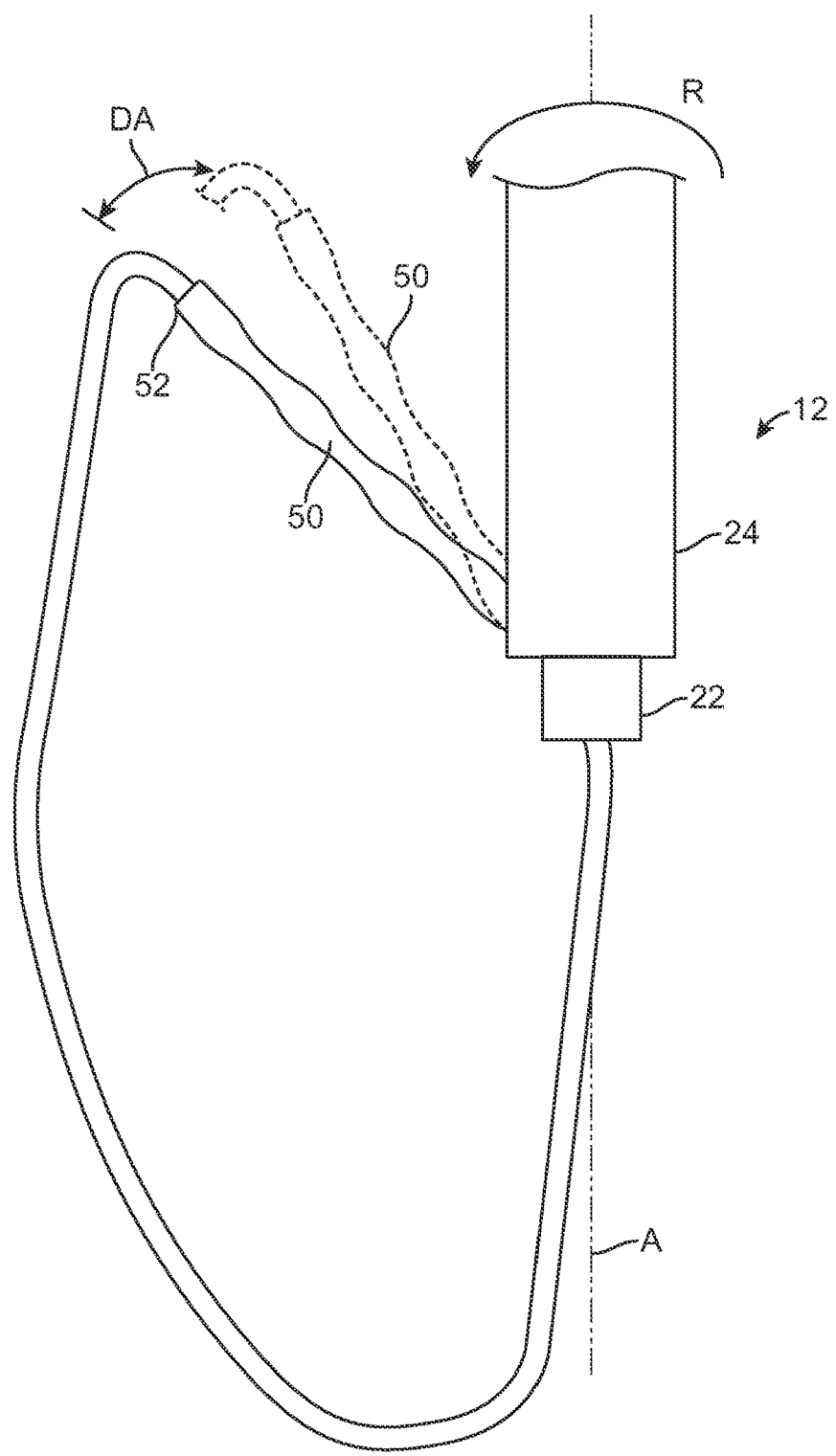
FIG. 8 shows the elbow being deflected proximally when the support shaft is rotated while the elbow contacts the lens.
Figure 9:
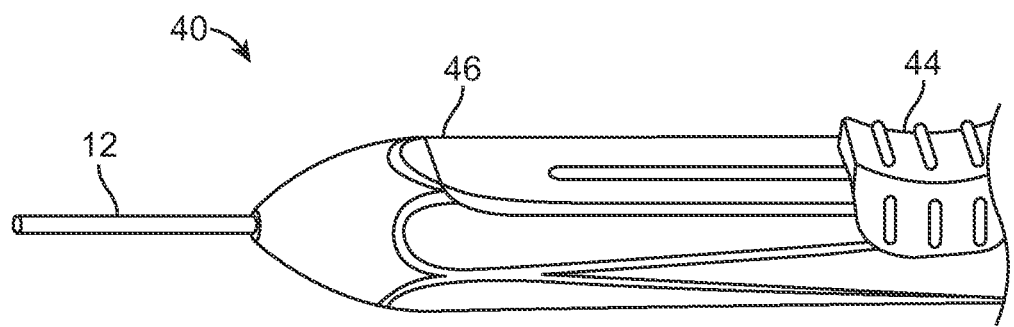
FIG. 9 shows another device for cutting a lens with a first actuator for the first end and a second actuator for the second end of the elongate element.
Figure 10:
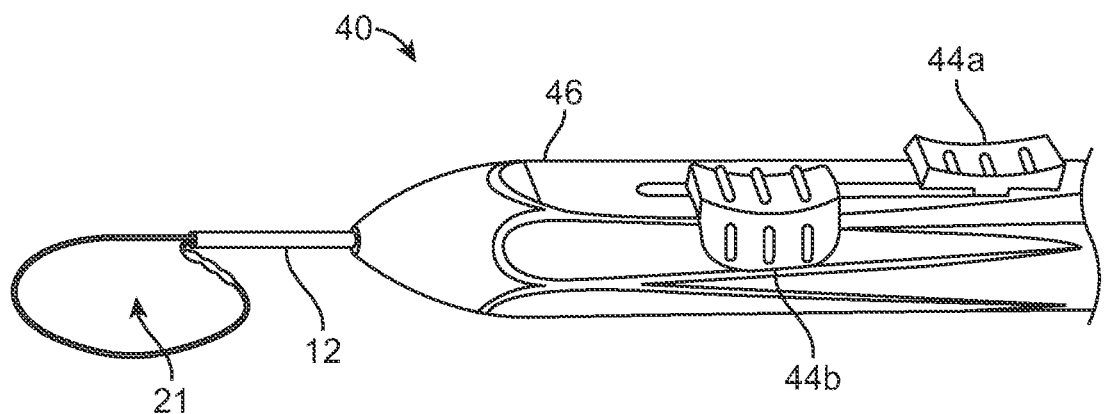
FIG. 10 shows the device of FIG. 9 with the loop expanded.

FIGS. 6-8 illustrate an interrelated device for cutting a lens. The device includes an elongate element 16 having an elbow 50 configured to be attached or integrally formed with the support shaft 12. The device 40 may be include the irrigation and aspiration features as described elsewhere herein as well as one or more actuators 44. The support shaft 12 can have a first or inner tube 22 with a first lumen 24 and a second or outer tube 26 with a second lumen 28. The second end 19 of the elongate element 16 extends through a space between the inner tube 22 and the outer tube 26 (see dotted line position of FIG. 4) or through the first lumen 24 (solid line position). The elongate element 16 may have a pre-shaped portion 32 and an unshaped portion 34 with all features and aspects described herein incorporated for this and all other devices and embodiments having pre-shaped, unshaped and straight portions.

The elongate element 16 has an elbow 50 at the first end 17 with the elbow 50 extending proximally from the support shaft 12 when the loop 21 is in the expanded position and optionally in the collapsed position as well. The elbow 50 provides a different stiffness response depending on the direction of the applied force in an advantageous manner. The loop 21 generally defines a loop plane LP in the expanded position with the loop plane LP being defined by an orientation that maximizes the size of the loop 21 in the expanded position. The elbow 50 may be at least twice as flexible in bending for a force applied to a tip 52 of the elbow 50 and lying in the loop plane LP compared to a force applied to the tip 52 of the elbow 50 and directed transverse to the loop plane LP. In this manner, the elbow 50 may be flexible to permit bending toward the support shaft 12 so that the elbow 50 may be "tucked" between the support shaft 12 and the lens L as described below. On the other hand, the elbow 50 is more stiff in the transverse direction (to the loop plane) which provides strength to the elongate element 16 (and an end of the loop 21) when manipulating the loop 21 around the lens L and, in particular, when sweeping the loop 21 around the posterior side of lens L to dissect the posterior surface PS of the lens L from the capsular bag.

The elbow 50 may be made of any suitable polymer and may include a living hinge, preferably at least two, formed by crimping the elbow 50 to form a crimped portion (FIGS. 7 and 8). The elbow 50 may be attached to the support shaft 12 (such as to the second tube 26) or may be integrally formed with the support shaft 12 as shown or advanced through the support shaft 12 as described below. The elbow 50 has an unbiased shape such that when the loop 21 is in the expanded position and the elbow 50 is released from constraining forces applied by the device, the elbow 50 moves proximally relative to the support shaft 12. Stated another way, the elbow 50 is oriented 90-180 degrees from a distal orientation of the support shaft 12 defined by a longitudinal axis A of the support shaft 12 at the distal end in the expanded position and optionally the collapsed position as well. In use, the support shaft 12 may be rotated in direction of arrow R about the longitudinal axis A with the elbow 50 in contact with the lens L. Rotation of the support shaft 12 in this manner deflects the elbow 50 toward the support shaft 12 and displaces the loop 21 proximally. Rotation of the support shaft 12 in this manner also moves the elbow 50 to a position between the support shaft 12 and the lens L. The elbow 50 is deflected to be in a more proximal orientation such as by reducing the angle between the tip orientation and the proximal direction defined by the longitudinal axis A of the support shaft 12. FIG. 8 shows a reduction in this angle by angle DA. The elbow 50 provides enhanced flexibility in bending toward the shaft 12 so that an angle between the support shaft 12 and the elbow 50 can be reduced by at least 30 degrees. The elbow 50 can be in contact with the lens so that the lens deflects a tip 52 of the elbow 50 toward the support shaft 12 and to a position between the support shaft 12 and the lens.

Figure 11:
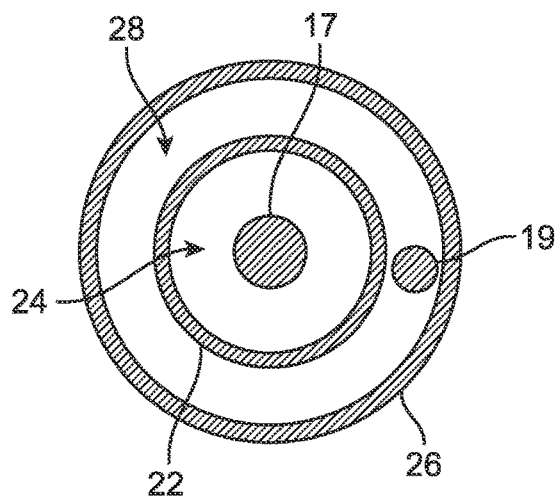
FIG. 11 shows a cross-sectional view of the device of FIG. 10.
Figure 12:
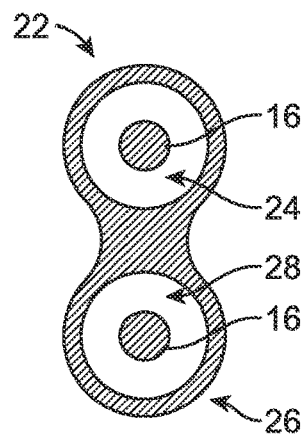
FIG. 12 shows an alternative cross-sectional view of the device of FIG. 10.
Figure 13:
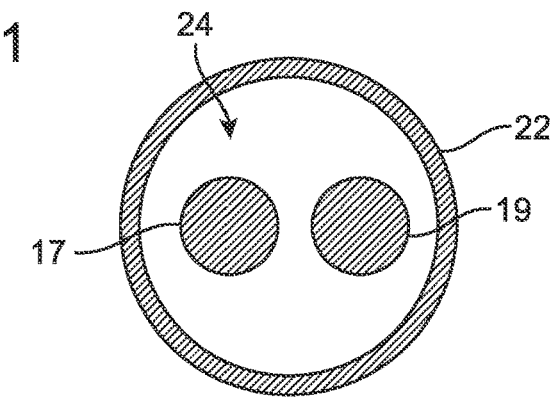
FIG. 13 shows still another alternative cross-sectional view of the device of FIG. 10.

FIGS. 9-15 show an interrelated implementation of a device 40 having an elongate element 16. As described previously, the elongate element 16 can have a first end 17 and a second end 19 that are both movable relative to the support shaft 12 to move the loop 21 between the collapsed and expanded positions. The first and second ends 17, 19 can be manipulated by one or more actuators 44. The actuator 44 can vary, including a button, slider, knob, or other mechanism. In some implementations, the actuator 44 can include a first controller 44a and a second controller 44b, respectively. The support shaft 12 may have various different cross-sectional arrangements. FIG. 11 shows a first tube 22 having a first lumen 24 and a second tube 26 having a second lumen 28 with the first tube 22 extending through the second tube 26. FIG. 12 shows a first tube 22 having a first lumen 24 and a second tube 26 having a second lumen 28 that are independent or side-by-side. Referring to FIG. 13, a first tube 22 has a first lumen 24 with both ends 17, 19 of the elongate element 16 extending through the first lumen 24.

Figure 14:
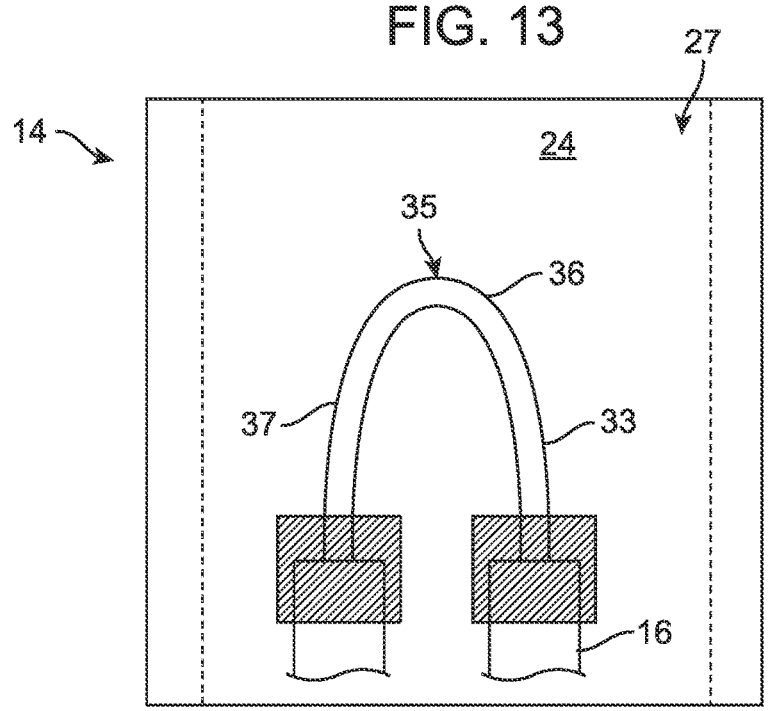
FIG. 14 shows an end of a support shaft with the elongate element having a flexible portion that can be folded and contained in the lumen as shown.

Referring to FIG. 14, the distal end 14 of the support shaft 12 is shown in cross-section with the elongate element 16 folded at a flexible portion 36 so that the elongate element 16 is fully contained in the first lumen 24. It is understood that when discussing one of the embodiments with dual movement that all aspects are equally applicable to the other and incorporated expressly for each.

The flexible portion 36 is folded to form a U-shape when the loop 21 is in the collapsed position as shown in FIG. 14. The flexible portion 36 may be small enough to fit within the first lumen 24 as shown. Even when the flexible portion 36 extends through separate lumens they can be positioned closely together thereby still helping to reduce the overall size of the device 40. The flexible portion 36 has a first half 33 extending toward the first end 17 and a second half 37 extending toward the second end 19 of the elongate element 16. The support shaft 12 can include the first lumen 24 with the flexible portion 36 contained within the first lumen 24 near the opening 27 when the loop 21 is collapsed. The flexible portion 36 can have a radius of curvature when in the folded position of less than 0.012 inch. The flexible portion 36 can be at least twice as flexible in bending as the first and second ends 17, 19 of the elongate element 16. The flexible portion 36 may have a maximum outer dimension of no more than 0.003 inch and may be a monofilament bonded to a superelastic element, such as a nitinol wire having a diameter of about 0.005 inch. Other suitable materials, cross-sections and sizes are considered herein, including larger sizes than those recited. The flexible portion 36 may also be defined as having a folded lateral dimension that is no more than 2.5 times the outer dimension of the two sides of the fold combined. As an example, if a 0.010 inch diameter wire is used the folded lateral dimension is no more than 0.025 resulting in a gap of no more than 0.005 inch. Stated still another way, the lumen 24 can have an inner diameter that is no more than 2.5 times the outer dimension of the two halves 33, 37 of the fold combined.

Figure 15:
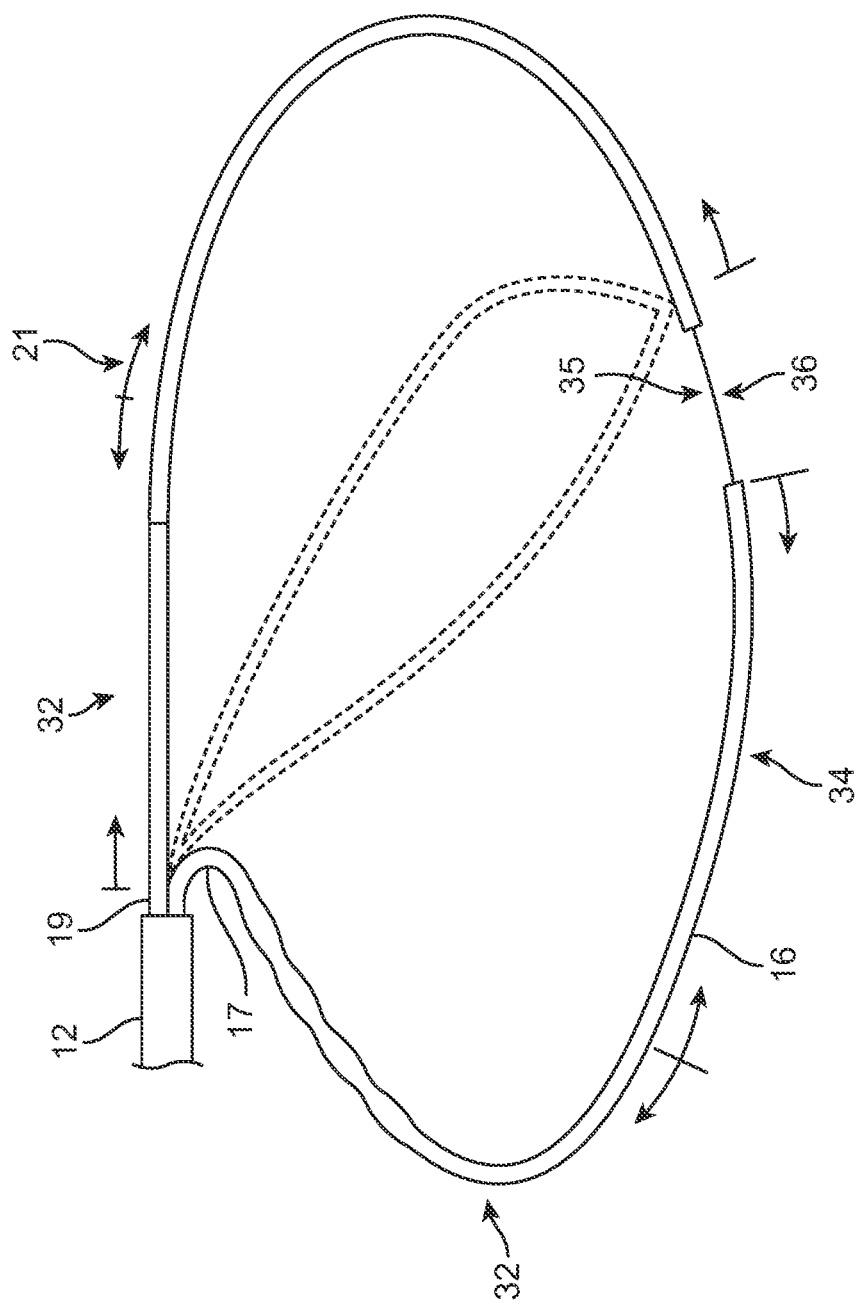
FIG. 15 shows the shaped and unshaped parts of the loop.
Figure 17:
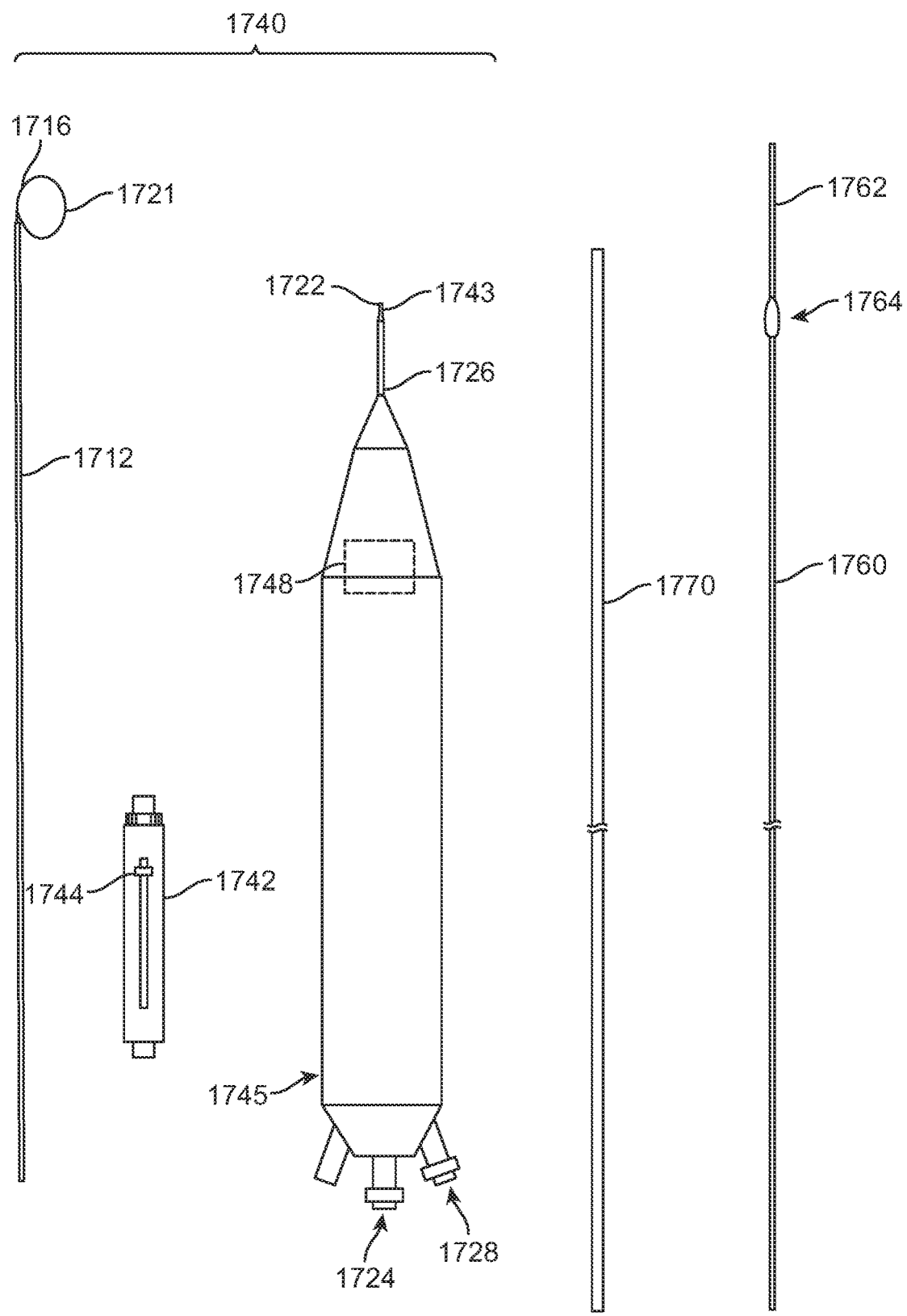
FIG. 17 shows a device for cutting a lens with a loop in conjunction with phacoemulsification.
Figure 18:
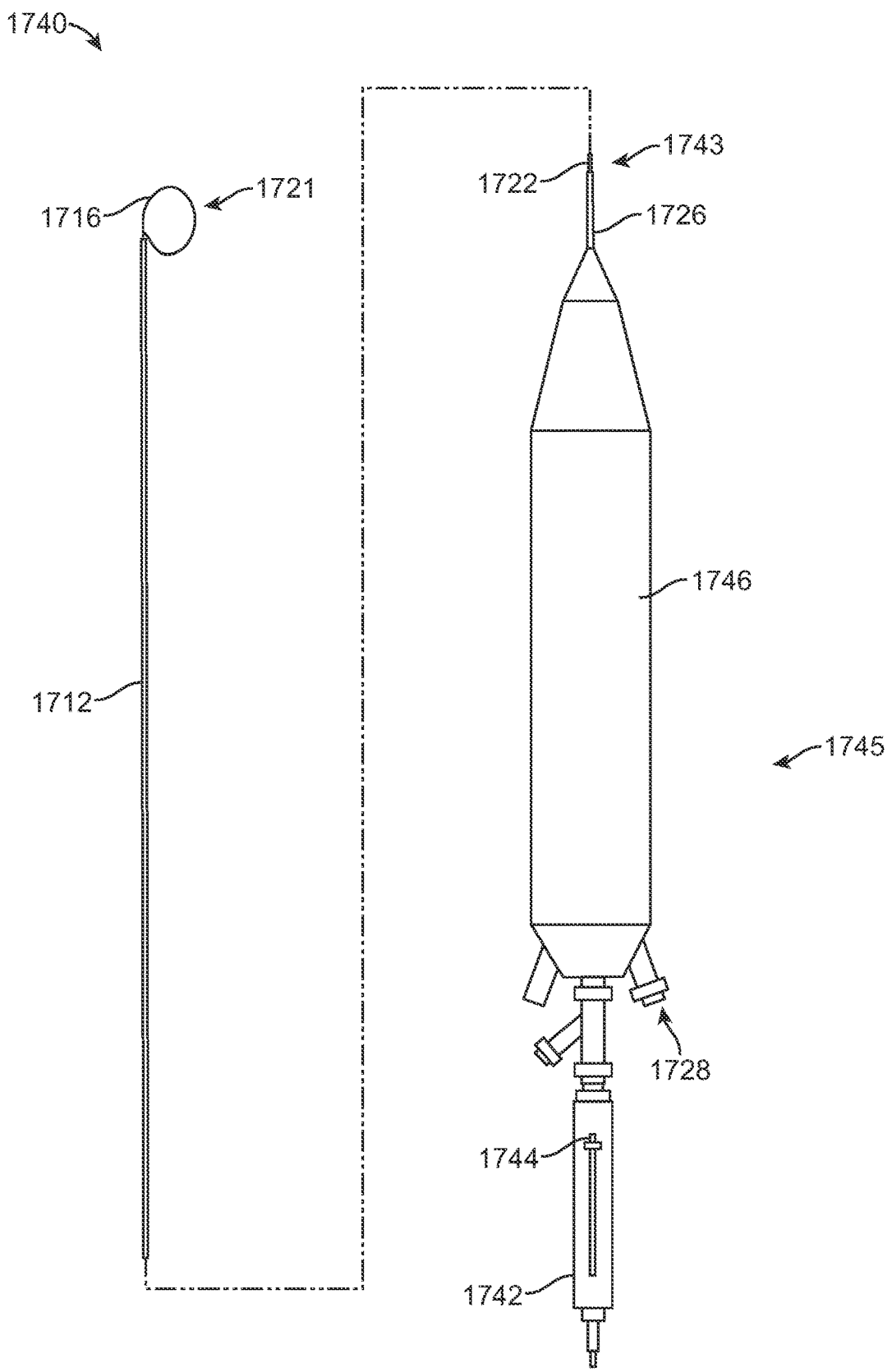
FIG. 18 shows the controller mounted to the aspiration lumen and the support shaft prior to backward loading of the support shaft.

The device 40 also may be advanced in a manner that establishes a distal portion of the loop 21 early in the deployment. As shown in FIG. 15, when the loop 21 is expanded, the elongate element 16 can have a total length that can be split into a first half 33 extending from the first end 17 to a midpoint 35 (and defining a first length) and a second half 37 extending from the second end 19 to the midpoint 35 (defining a second length). Furthermore, an intermediate loop can be formed when half of the total length has been deployed. When in the intermediate position, the entire loop 21 can be positioned distal to a distal end 14 of the support shaft 12. The first and second ends 17, 19 of the elongate element 16 may both be movable relative to the support shaft 12 to move the loop 21 from the collapsed position to the expanded position. When deploying the loop 21 distally, only one end of the elongate element 16 may be moved although the other end may be moved as well.

The forwardly extending loop 21 in the intermediate position can be formed by advancing the second end 19 between the capsular bag and the lens in a distal direction toward an opposing edge position. The opposing edge position can be at least 90% of a radius of the lens and may also be within 60 degrees of the opposing edge defined as a projection of the longitudinal axis A of the support shaft 12 to the circumference C of the lens L when viewed along a central axis CA of the lens L.

Still with respect to FIG. 15, the elongate element 16 of the device also may have a pre-shaped portion 32 and an unshaped portion 34 and all aspects of the pre-shaped 32 and unshaped portions 34 described herein are applicable here.

For example, the pre-shaped portion 32 may be 40%-75% of the total length and the unshaped portion 34 may be 25%-60% of the total length. Furthermore, the elongate element 16 may be formed so that at least 80% of the unshaped portion 34 is along a first half. The elongate element 16 has a total length in the expanded position with a first half, which extends from the midpoint 35 toward the first end 17, and a second half, which extends from the midpoint 35 toward the second end 19. The shaped portion 32 may be substantially deployed along the second half (which may also include the pre-shaped elbow 50) so that at least 80% of the pre-shaped portion 32 is along the second half while at least 80% of the unshaped portion 34 is along the first half. The first half includes primarily a proximal half of the loop 21 while the second half includes primarily a distal half of the loop 21, which is split geometrically with a transverse division relative to the longitudinal axis A. In the intermediate position, the deployed portion of the second half can be shaped throughout while the first half can include at least part of the unshaped portion 34 in the intermediate position and may be at least 50% unshaped in the intermediate position.

As with other implementations described herein, the first end 17 may also include an elbow 50 extending proximally from the support shaft 12 when the loop 21 is in the expanded position and all aspects and uses of the elbow 50 are expressly incorporated here. The elbow 50 is not yet deployed when the loop 21 is in the intermediate position so that the forwardly extending intermediate loop is not impeded. When the elbow 50 is partially deployed, the elbow 50 can be then carefully tucked between the lens and the capsular bag. The elbow 50 can be deflected proximally into the space between the capsular bag and the lens by rotating the support shaft 12 to displace the elbow 50 of the elongate element 16. As the elbow 50 is rotated, the lens deflects the elbow 50 to be more proximally oriented relative to the support shaft 12. The first end 17 of the elongate element 16 may be advanced while rotating the support shaft 12.

As mentioned, the actuator 44 can include first and second controllers 44a, 44b. The first and second controllers 44a, 44b may also be moved together, or locked together, for simultaneous movement. It should be appreciated movement of both ends of the elongate element 16 is considered herein. For example, advancing both ends 17, 19 simultaneously will still yield an intermediate position satisfying the aspects described above, and incorporated here, related to the intermediate position.

The elongate element 16 may also be removed from the device 40 and, in particular, from the first and/or second lumens 24, 26, so that the first and/or second lumens 24, 26 may be used for irrigation and/or aspiration. To this end, at least one of the first and second ends 17, 19 is releasable from the actuator 44 and may be withdrawn by manipulating the other end to withdraw the free end into the device 40. The elongate element 16 may be completely removed from the first and/or second lumens 24, 26 so that the elongate element 16 is not positioned within the lumen. In this manner, the first and second lumens 24, 26 are not obstructed by the elongate element 16 for aspiration and/or infusion. The elongate element 16 may be withdrawn without removing the support shaft 12 from the eye. The device 40 may be removed from the eye and the elongate element 16 removed and the same device 40 reintroduced or a separate device introduced.

FIGS. 16A and 16B show the device 40 having an angled portion 42 near its distal end of the support shaft 12, the angled portion 42 having an angled distal tip 43. The angled, distal tip 43 of the angled portion 42 extends distal to the opening 27 through which the elongate element 16 exits the support shaft 12. The angled portion 42 has a proximal portion (extending proximally) and a distal portion (extending distally) and terminates at the angled tip 43. The proximal portion has a proximal orientation and the distal portion has a distal orientation defined by a proximal axis 105 and a distal axis 110, respectively, of a first lumen 24 in a first tube 22. A second tube 26 having a second lumen 28 extends over the first tube 22 with the second lumen 28 being used to irrigate the eye. The proximal and distal orientations lie in and define a working plane WP.

The support shaft 12 extends parallel to the second tube 26 and is positioned beneath the proximal portion of the second tube 26 to reduce obstruction of the field of view compared to side by side lumens. The support shaft 12 extends to a position adjacent to and somewhat offset from the proximal portion so that, in use, the loop 21 extends beneath the proximal portion. The loop 21 generally defines a loop plane LP in an orientation that maximizes an area bounded by the expanded loop 21. The loop 21 is positioned around the lens L with the working plane WP being oriented less than 45 degrees, or less than 20 degrees, from the loop plane LP when the loop 21 is in the expanded position. Stated another way, the angled portion 42 is directed away from the loop 21 and the lens L to reduce the likelihood that the sharp tip 43 damages the eye when manipulating the loop 21.

Referring to FIG. 16C, the device 40 may also have a support shaft 12 that includes an angled portion 42. The angled portion 42 can have a proximal portion (extending proximally) and a distal portion (extending distally) and terminates distally at the angled tip 43. The proximal portion has a proximal orientation and the distal portion has a distal orientation defined by a proximal axis 105 and a distal axis 110, respectively. The support shaft 12 may also include a second tube having a second lumen with the first tube extending through the second lumen as described elsewhere herein. The elongate element 16 (and loop 21) can be advanced and withdrawn through opening 27. The proximal and distal orientations can lie in and define a working plane WP. The loop 21 generally defines a loop plane LP in an orientation that maximizes an area bounded by the expanded loop 21. When the loop 21 is in the expanded position and is positioned around the lens L the working plane WP is oriented less than 45 degrees, or less than 20 degrees, from the loop plane LP. The distal end of the angled tip 43 can be directed away from the loop 21, and the lens L, for the reasons previously mentioned.

Still with respect to FIGS. 16A-16C, the device 40 can also include a flexible portion 36 that is folded to form a folded portion when the loop 21 is in the collapsed position so that the folded portion may be small enough to fit within the second lumen 28. The device 40 also may be advanced in a manner that establishes a distal portion of the loop 21 early in the deployment (as discussed above with respect to FIG. 15) and all such methods are expressly incorporated here and in all other embodiments which may incorporate this method including the distribution and aspects related to the shaped and unshaped portions 32, 34 of the elongate element 16. When the loop 21 is expanded, the elongate element 16 can have a total length that can be split into a first half extending from the midpoint 35 toward the first end 17 (defining a first length) and a second half extending from the midpoint 35 toward the second end 19 (defining a second length). Furthermore, an intermediate loop is formed when half of the total length has been deployed with the intermediate loop positioned distal to the opening 27 in the support shaft 12 and specifically the second tube 28 as shown in FIG. 16A.

The first and second ends 17, 19 of the elongate element 16 may both be movable relative to the support shaft 12 to move the loop 21 from the collapsed position to the expanded position. Furthermore, the first end 17 may include an elbow 50 extending proximally from the support shaft 12 when the loop 21 is in the expanded position and all aspects and uses of the elbow 50 are expressly incorporated here. For example, the elbow 50 may be partially deployed (such as in an intermediate position) and then tucked between the lens and the capsular bag. The elbow 50 may then be fully deployed and rotated as described above to deflect the elbow 50 to be more proximally oriented. The elongate element 16 may also have a pre-shaped portion 32 and an unshaped portion 34 and all aspects of the pre-shaped portion 32 and unshaped portion 34 described herein are applicable here. For example, a pre-shaped portion 32 may be 40%-75% of the total length and the unshaped portion 34 may be 25%-60% of the total length. Furthermore, the elongate element 16 may be formed so that at least 80% of the unshaped portion 34 is along a first half and with the forward extending portion at least 80% of the unshaped portion 34 is along the second half.

As mentioned above, the devices described herein may be used independently or as a part of or in conjunction with a fluid handling device 140 (shown in FIG. 1). The elongate element 16 may also be removed from the fluid handling device 140 and, in particular, from the second lumen 28, so that the lumen 28 may be used for irrigation or aspiration. To this end, the device 40 is simply withdrawn through the second lumen 28 and may be completely removed from the second lumen 28. The device 40 also may be removed from the eye and the elongate element 16 removed from the device 40.

FIGS. 17-31 show an interrelated implementation of the device for cutting a lens configured to be used in conjunction or in combination with a phacoemulsification hand piece 1745. The device 1740 can have a support shaft 1712 and an elongate element 1716 that forms a loop 1721. The support shaft 1712 can have a lumen 1724 and the elongate element 1716 can extend through the lumen 1724. The hand piece 1745 can have a housing 1746 with a tip 1743 extending from the housing 1746 to a distal end 1714. The tip 1743 can be coupled to a vibrating element 1748 mounted to the housing 1746 for vibrating the tip 1743. A first lumen 1724 can extend through the tip 1743 to an opening 1727 near the distal end 1714 of the shaft 1712. The tip 1743 can be vibrated to break the lens L into fragments. Fluid and the lens fragments may be removed using the first lumen 1724 using aspiration, as will be described in more detail below.

The elongate element 1716 can be moved and advanced outwardly from the tip 1743 such as from the first lumen 1724. The tip 1743 can include a first tube 1722 that extends to the distal end 1714 and has the first lumen 1724. The tip 1743 may also include a second tube 1726 positioned around the first tube 1722 with the second tube 1726 having a second lumen 1728. The second tube 1726 may be a polymer sheath and the first tube 1722 may be a metallic tube. The elongate element 1716 may be removed from the eye without withdrawing the distal end of the tip 1743 from the eye.

Figure 19:
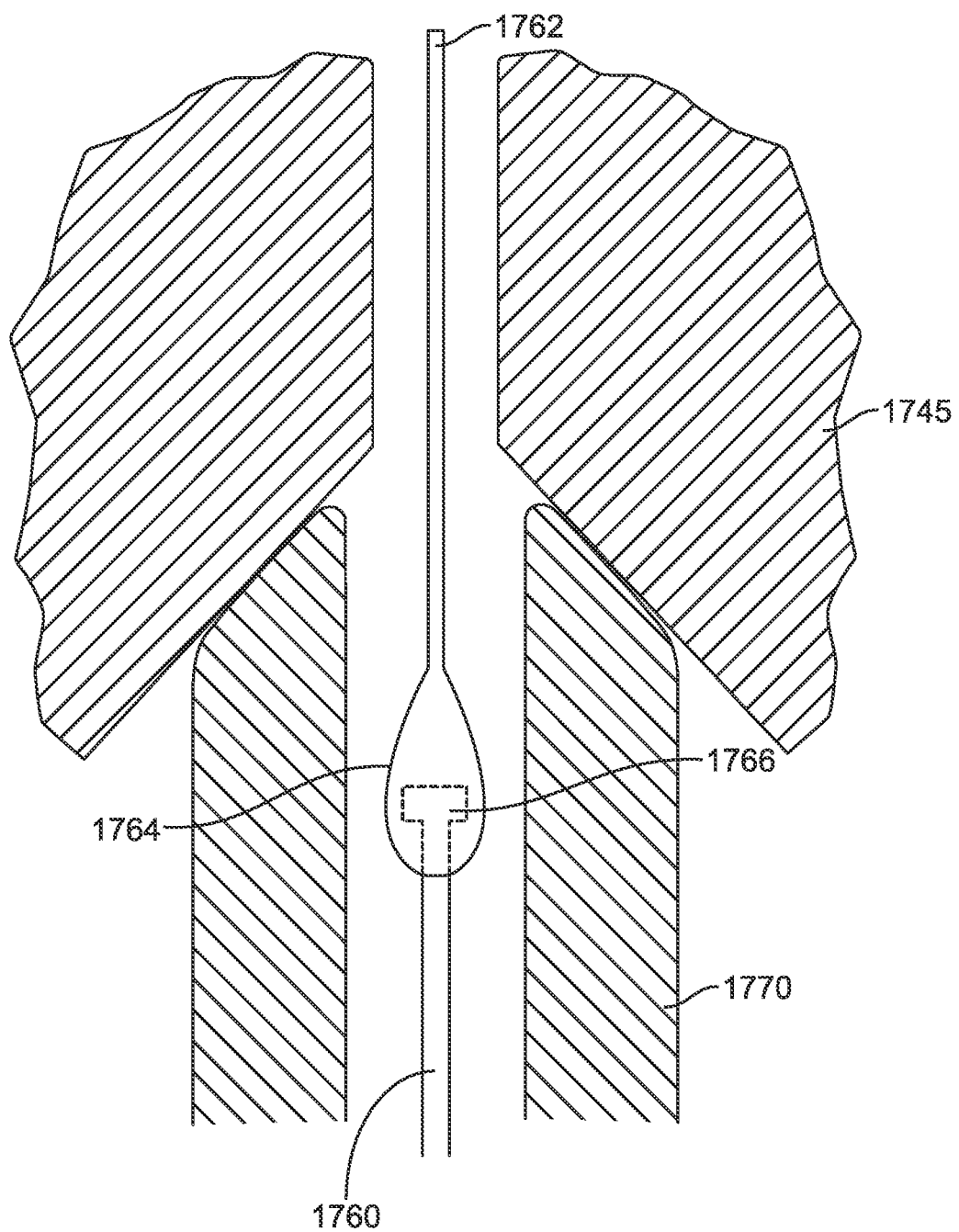
FIG. 19 is a cross-sectional view showing a transition in the aspiration lumen.
Figure 20:
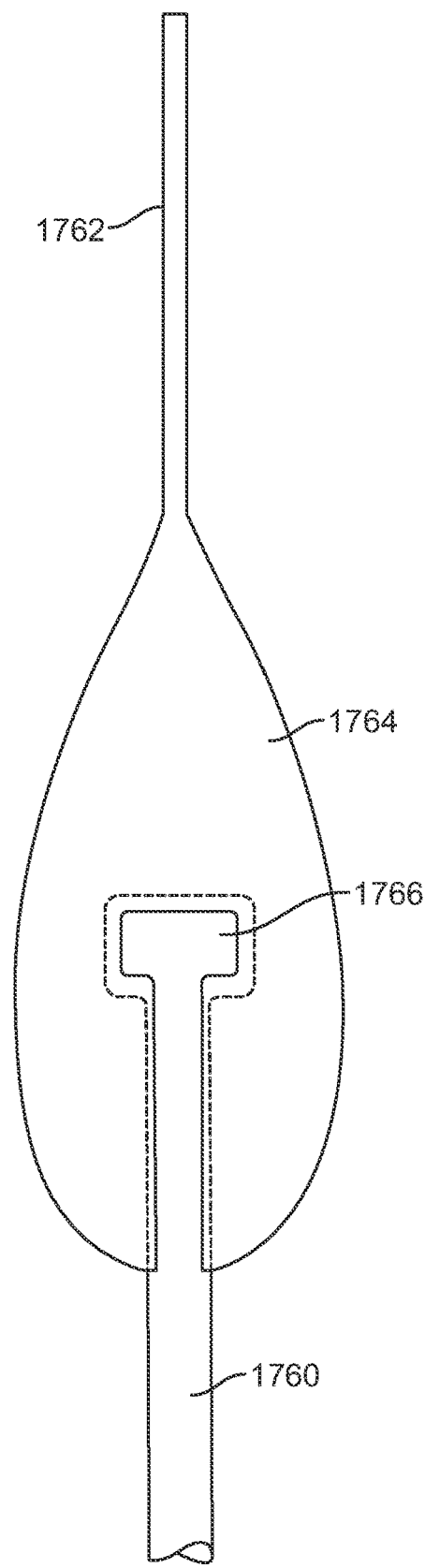
FIG. 20 shows the introducer having a leading filament which may be removed prior to attaching the support shaft to the introducer.

As with other implementations, the device 1740 can include one or more actuators 1744 that can be incorporated with a controller 1742 configured to be coupled to the elongate element 1716. The controller 1742 can be operable to change a size of the loop 1721 by manipulating the elongate element 1716. The controller 1742 and the elongate element 1716 may be initially separated with the elongate element 1716 being coupled to an introducer 1760. The introducer 1760 can be advanced distally through the first lumen 1724 until a distal end of the introducer 1760 extends from the opening 1727 near the distal end 1714 of the first lumen 1724, for example at the distal end of the tip 1743. The introducer 1760 may have a leading filament 1762, which is removed when the introducer 1760 has been advanced through the distal end 1714. The elongate element 1716 can be coupled to the introducer 1760 extending beyond the distal end 1714 by a coupler 1764. The elongate element 1716 can be introduced into the first lumen 1724 in a proximal direction by moving the introducer 1760 proximally into the first lumen 1724 and pulling the elongate element 1716 along with it in a proximal direction. As shown in FIG. 19, a guide 1770 may also be used to direct the relatively small introducer 1760 to a reducer section in the phacoemulsification hand piece 1745. The guide 1770 may be removed once the introducer 1760 has been advanced to the tip 1743.

Removal of the elongate element 1716 from the first lumen 1724 provides for unimpeded function of the first lumen 1724 for removing lens fragments and fluid once the lens has been cut. The phacoemulsification tip 1743 may remain in the eye while the loop 1721 is withdrawn and removed. The elongate element 1716 may be withdrawn by itself or with the controller 1744 without requiring removal and reintroduction of the tip 1743 of the phacoemulsification hand piece 1745.

The phacoemulsification hand piece 1745 may also incorporate the angled tips 43 of FIGS. 16A-16C. To this end, the orientation of the tip 43, the working plane WP, and the loop plane LP may include the features described above along with other aspects of the method related to FIGS. 16A-16C which are all incorporated here. A support shaft 1712 of the phacoemulsification hand piece 1745 includes a first tube 1722 having a first lumen 1724. The first end 1717 and the second end 1719 of the elongate element 1716 extend through a second lumen 1728 in a second tube 1726 and specifically in a space between the first and second tubes 1722, 1726. The second tube 1726 also has an opening 1727 in a sidewall with the first and second ends 1717, 1719 of the elongate element 1716 extending through the opening 1727 when the loop 1721 is in the expanded position. The elongate element 1716 may be removed from the eye by withdrawing the elongate element 1716 into the hand piece 1745 and even removed completely from the second lumen 1728. A fluid may also be delivered to the eye through the second lumen 1728 which may provide sufficient lumen area for fluid delivery even when the elongate element 1716 is positioned in the second lumen 1728.

The angled portion can have a proximal portion and a distal portion. The distal portion can extend distally and terminate at a distal tip 1743 of the angled portion. The proximal portion of the angled portion can have a proximal orientation and the distal portion can have a distal orientation defined by a proximal axis and a distal axis, respectively, of the first lumen 1724. The proximal and distal orientations can lie in, and define, a working plane WP. The loop 1721 can generally define a loop plane LP, which is determined by an orientation that maximizes an area bounded by the loop 1721 in the expanded position. The loop 1721 can be positioned with the working plane WP oriented less than 45 degrees, or less than 20 degrees, from the loop plane LP when the loop 1721 is in the expanded position and the loop plane LP is parallel to the midplane of the lens L. In this manner, the distal tip 1743 of the angled portion can be directed away from the loop 1721 when the loop 1721 is in the expanded and the tip 1743 remains clear of the capsular bag when manipulating the loop 1721 around the lens. Stated another way, the loop 1721 can be positioned with the distal end of the angled tip pointing away from the lens L when the loop 1721 is moved into position around the lens prior to cutting the lens. Finally, rather than defining the relationship between the working plane WP and the loop plane LP, the relative orientation may be described as an offset angle of 90 to 180 degrees. The offset angle is the angle which the tip 1743 is rotated from an origin (zero degrees) position in which the loop plane LP is substantially parallel to the working plane WP and the tip 1743 is directed at, and essentially in, the loop 1721 at 0 degrees. The tip 1743 can be preferably oriented so that the offset angle is 90 to 180 degrees which directs the tip 1743 away from the capsular bag as mentioned above.

The loop 1721 may also be positioned with the first end 1717 of the elongate element 1716 attached to the second tube 1726 of the phacoemulsification device in the same manner as described above and such aspects are expressly incorporated here for all purposes.

Figure 21:
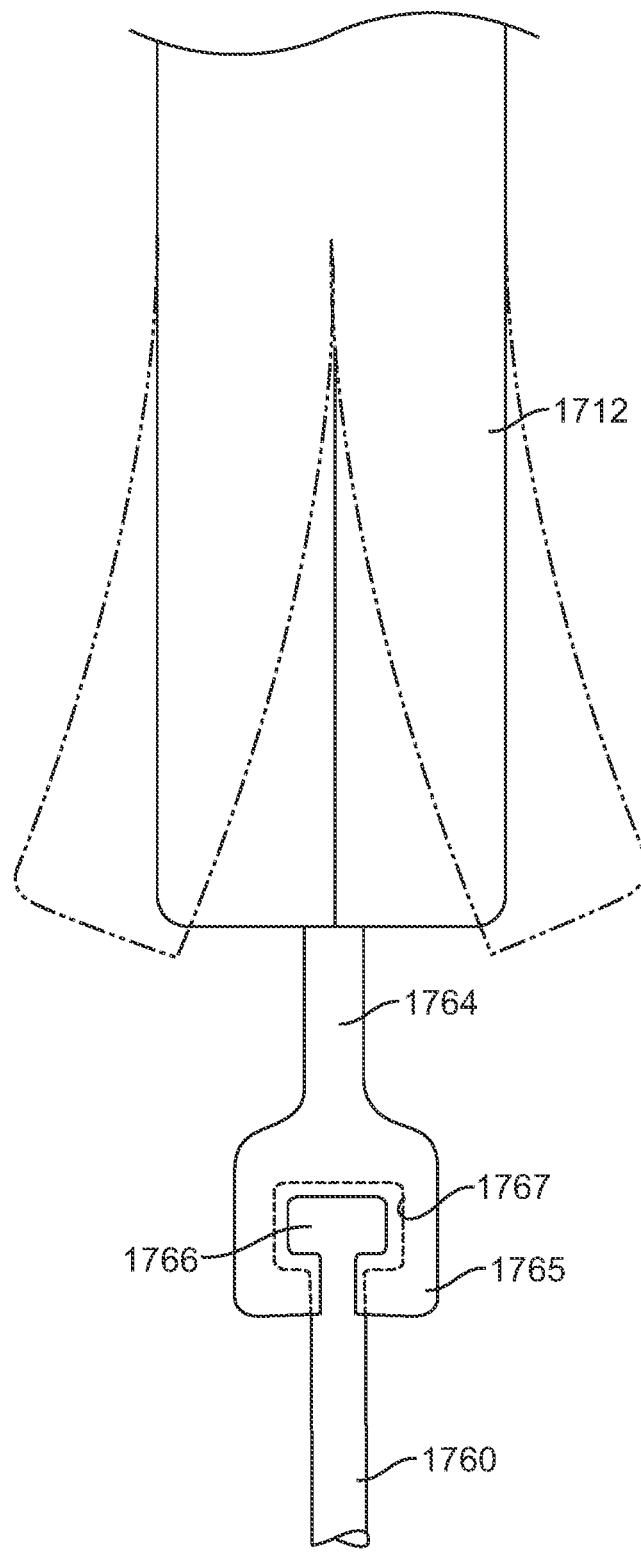
FIG. 21 shows the proximal end of the support shaft with the support shaft being split.
Figure 22:
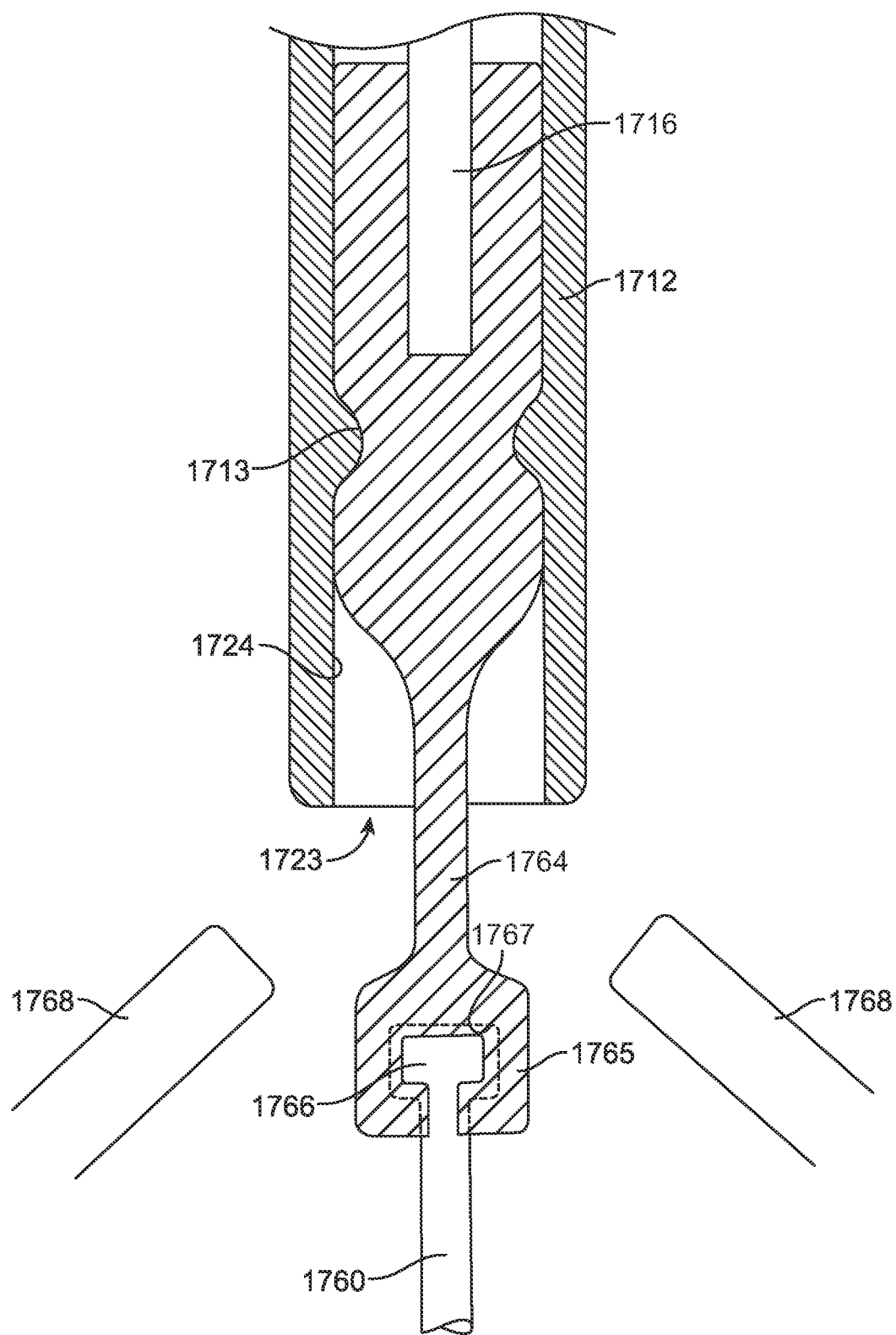
FIG. 22 is a cross-sectional view of FIG. 21 showing a coupler held by the support shaft.
Figure 23:
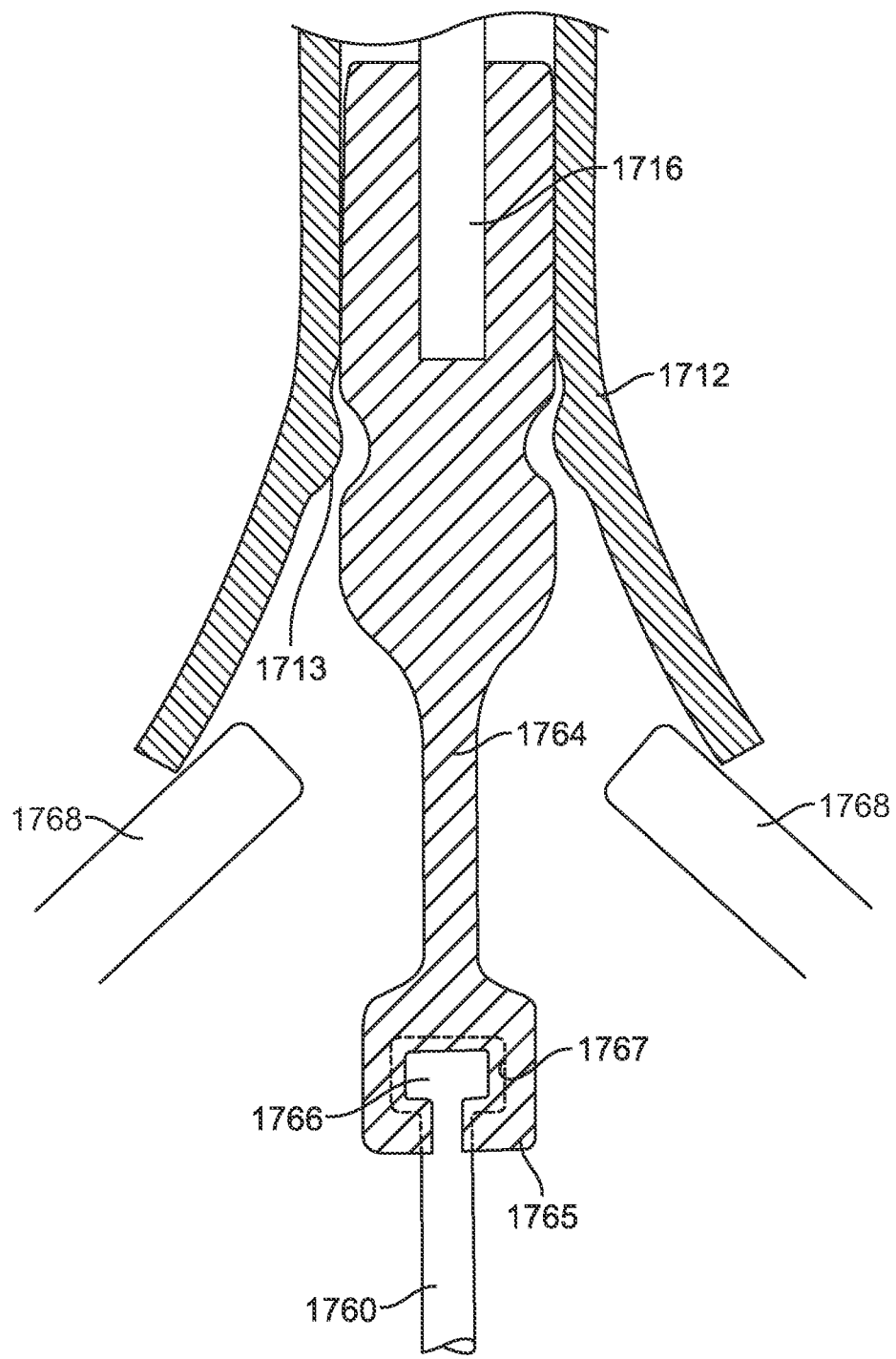
FIG. 23 shows release arms moved into position to open the proximal end of the support shaft along the split.
Figure 24:
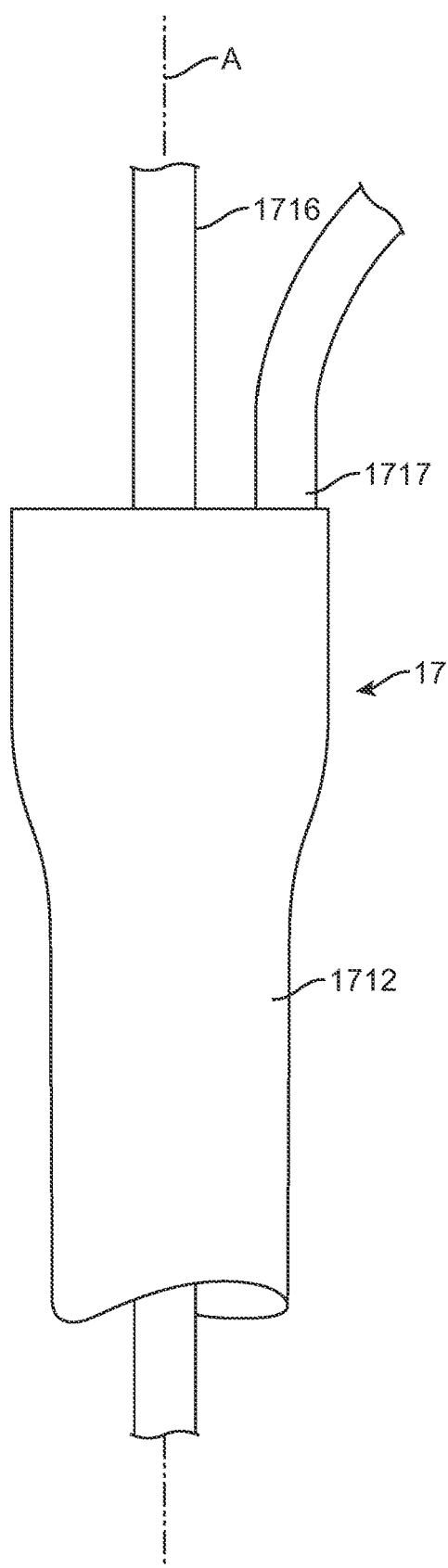
FIG. 24 shows the distal end of the support shaft with the elongate element.
Figure 25:
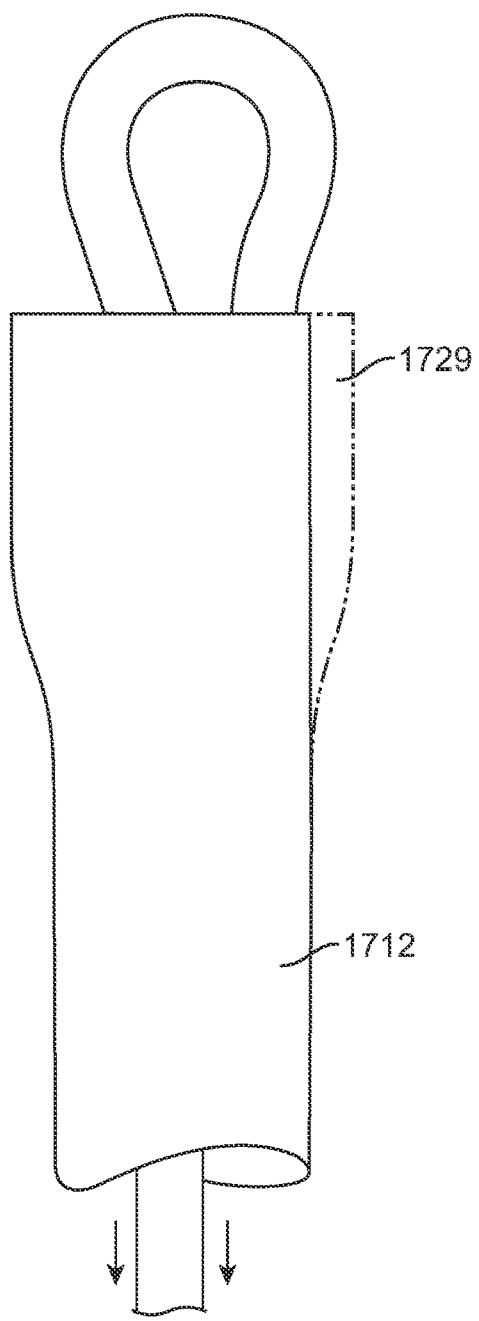
FIG. 25 shows the elongate element withdrawn into the lumen that causes the support shaft to reduce in dimension to permit withdrawal of the support shaft.
Figures 26, 27:
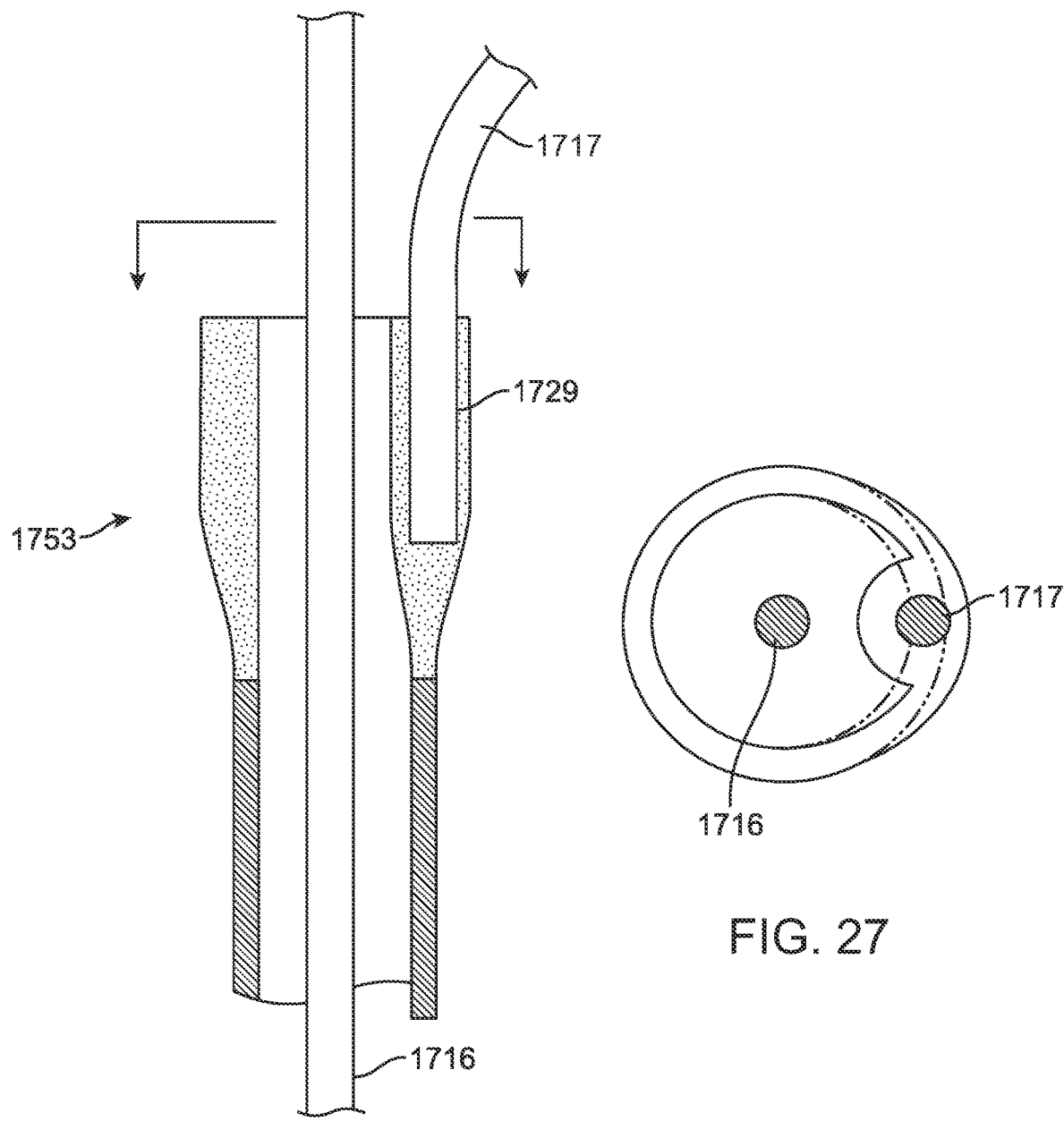
FIG. 26 shows a cross-sectional view of FIG. 25.
FIG. 27 shows a cross-sectional view of the support shaft showing the decrease in dimension.
Figure 31:
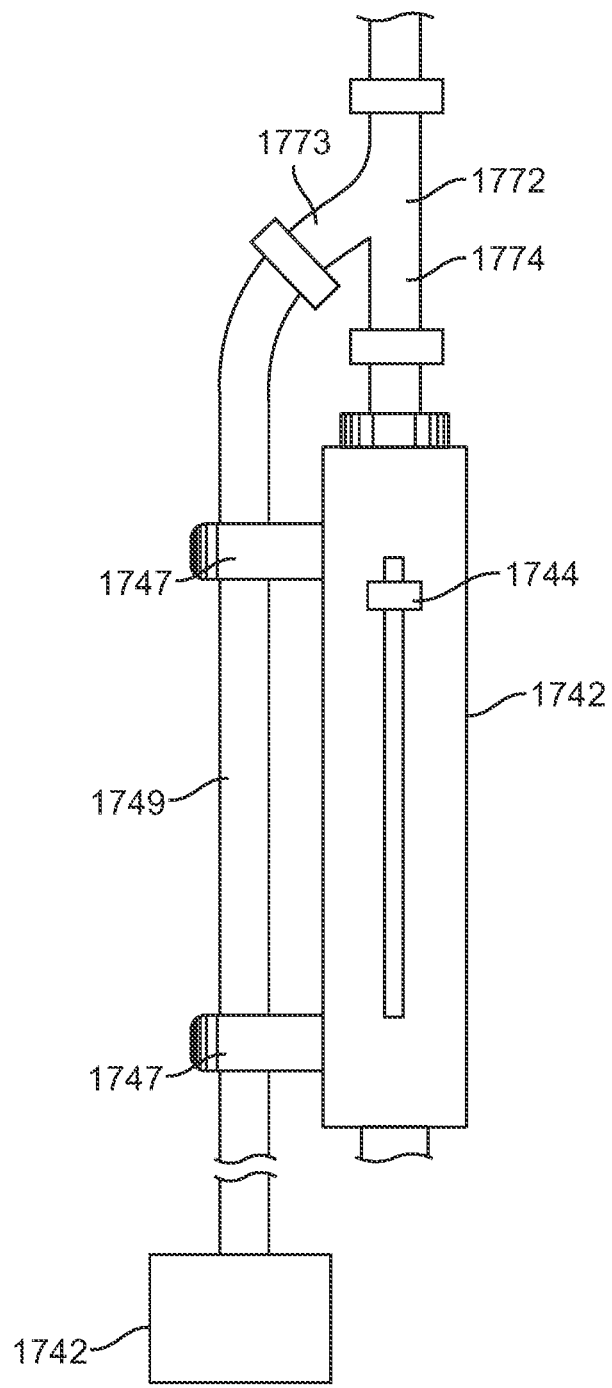
FIG. 31 shows the controller attached to a tube extending proximally from the hand piece.

Referring to FIGS. 21-23, the coupler 1764 can be attached to the introducer via coupling 1766. The introducer 1760 can then be used to backload the elongate element 1716 and support shaft 1712 into the first lumen 1724 of the first tube 1722. The coupler 1764 can have a block 1765 having a recess 1767 that receives a lip 1713 on an inner surface of the support shaft 1712. The support shaft 1712 can split at a proximal end to release the block 1765 as described below. FIG. 22 shows the proximal end opening 1723 of the support shaft 1712. FIG. 23 shows the proximal end opening 1723 of the support shaft 1712 after being opened along the split to release the block 1765. FIG. 21 also shows a support shaft 1712 opened along a split in the dotted-line position. The support shaft 1712 can be opened with a release arm 1768 or pair of release arms 1768 engaged with each side of the support shaft 1712 defined by the split. The release arms 1768 can engage the support shaft 1712 to force the two sides of the shaft 1712 apart along the split as shown in FIG. 23. The coupler 1764 can be released from the shaft 1712 in this manner. The release arms 1768 can be movable into the release position and once in the release position, the release arms 1768 may remain stationary while the support shaft 1712 is moved into engagement with the arms 1768. The coupler 1764 can then be locked to the controller 1742 so that the actuator 1744 can be used to move the coupler 1764 and, therefore, the elongate element 1716. The arms 1768 or both the arms 1768 and the shaft 1712 may be movable. The coupler 1764 may be releasably attached to the shaft 1712 in any other manner.

Referring now to FIGS. 24-27, the elongate element 1716 can include a stop 1729 at the first end 1717 that is in contact with the first tube 1722 during the cutting step to stabilize the first end 1717 of the elongate element 1716. Stabilizing the cutting device within the tube permits manipulation of the device with the outer tube. For example, if the cutting device extends through a tube of a phacoemulsification device (or any other tube such as a cannula), it may be desired to manipulate the cutting device with the tube. As such, it may be advantageous to anchor the cutting device within the tube with the stop 1729. If the cutting device is back-loaded into the tube, the stop 1729 may also positively dictate the position of the cutting device in the tube. To this end, the stop 1729 may be sized for a modest interference fit with an inner wall of the first tube 1722. If the cutting device is designed for removal through the first tube, the stop 1729 may also be "unlocked" from the first tube so that the cutting device may be withdrawn and removed through the first tube. The configuration of the stop 1729 can vary. For example, the stop 1729 may form part of the support shaft 1712 as shown or the elongate element 1716 itself may be larger along the stop 1729 so long as the stop 1729 is associated with and attached to the elongate element 1716. The elongate element 1716 may be withdrawn into the first lumen 1724, and preferably completely removed from the first lumen 1724 after cutting the lens and without removing the tip 1743 from the eye. The stop 1729 may be reduced in size. For example, the stop 1729 can have a dimension, such as width, that decreases to decrease contact between the support shaft 1712 and the first tube 1722 (or tip) when withdrawn. Stated another way, the support shaft 1712 can have an enlarged portion 1753 when measured transverse to the longitudinal axis A of the support shaft 12. The enlarged portion 1753 can be larger than adjacent portions of the support shaft 1712. The first end 1717 of the elongate element 1716 can be attached to the support shaft 1712 at the enlarged portion 1753 of the support shaft 1712 forming the stop 1729. The enlarged portion 1753 of the support shaft 1712 can move to a radially reduced size (see FIG. 25) when the elongate element 1716 is withdrawn into the lumen 1724 of the support shaft 1712 to "unlock" the cutting device from the tube. The elongate element 1716 can displace the enlarged portion 1753 radially inward and away from the wall of the lumen 1724. The stop 1729 can be formed by the elongate element and the support shaft 1712. However, it may also be defined as being part of (an extension of) the elongate element 1716. For example, an elastomer collar may be attached to the elongate element which is then bonded to the end of the support shaft 1712. It should be appreciated that the stop 1729 may be defined as part of the elongate element 1716 or the support shaft 1712.

As best shown in FIGS. 28-31, the controller 1742 can include a clip 1747 configured to attach the controller 1742 to a fluid line 1749 that may extend from a proximal end of the hand piece 1745. The controller 1742 and its one or more actuators 1744 can be in an ergonomic position and permit the user to easily find and manipulate the actuators 1744 without having to look and may operate the controller 1742 with the free hand. A fluid Y-arm 1772 can be provided so that the support shaft 1712 can extend through the lumen 1724 for attachment to the controller 1742. The y-arm 1772 can include a main lumen that may be attached to a lumen in the hand piece 1745 such as the aspiration lumen 1724. The y-arm 1772 can split into a first leg 1773 and a second leg 1774 with the controller 1742 attached to one of the legs (1774 in FIG. 31) and a source 1742 of suction or vacuum coupled to the other leg 1773.

The one or more actuators 1744 of the controller 1742 can be coupled to the elongate element 1716 to move the elongate element 1716 between the collapsed position and the expanded position. The hand piece 1745 can include a housing 1746 and the controller 1742 can be attached to a tube or fluid line 1749 extending proximally from the housing 1746 using the one or more clips 1747. The controller 1742 can be positioned at a convenient location proximal to the hand piece 1745 for manipulation with the user's free hand.

It is understood that aspects of the methods and devices may be combined including all loop aspects as being clearly applicable to each delivery structure and, thus, all loop aspects may be practiced with, for example, the phacoemulsification device and such combinations are expressly included herein. For example, any of the first or second tubes described herein may be combined with the associated elongate elements to form a disposable product for the phacoemulsification devices (typically referred to as a "sheath"). The source of irrigation fluid may also form part of the product and all such combinations are also contemplated herein. Similarly, the controller and y-arm may form parts of a disposable product including any of the devices for cutting the lens described herein.

The devices are described as useful for cutting a whole lens within the capsular bag, but may be used for other purposes without departing from various aspects of the device and methods described. The elongate element may be positioned and extended between the capsular bag and the anterior side of the lens due to natural expansion of the elongate element toward the expanded shape. When cutting the lens, the loop may extend around the posterior and anterior surfaces to form a full cut of the lens. The elongate element may also be moved between the posterior surface of the lens and the capsular bag to dissect the lens from the capsular bag before cutting the lens into fragments. The devices described herein are particularly useful in advancing atraumatically between the bag and lens while the lens is still whole.

The terms "first" and "second" may be used interchangeably herein. For example, the first end of the elongate element may be shown as being attached to the support shaft and the second end movable relative to the support shaft. Furthermore, the support shaft may include the first tube and/or the second tube or it may be simply be a shaft without a lumen. The support shaft may be also be used interchangeably for more specific aspects of the support shaft such as the first tube or the second tube or the angled tip so long as the relationship to the elongate element is the same. Any of the elongate elements may be used with any of the other aspects of the devices (any support shaft) described herein and all such combinations are expressly incorporated. For example, any of the elongate elements or loops or aspects thereof may be used with the phacoemulsification hand piece or the irrigation and aspiration embodiments.

The devices and methods may be described in relation to preferred embodiments and it is understood that numerous modifications could be made to the preferred embodiments. For example, the elongate element may have additional filaments or cross-filaments without departing from numerous aspects described.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation, "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. However, such terms are provided to establish relative frames of reference, and are not intended to limit the use or orientation of an anchoring delivery system to a specific configuration described in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A device for cutting a lens in a cataract procedure comprising:
   a support shaft extending along a longitudinal axis between a proximal end and a distal end opposite the proximal end along the longitudinal axis; and
   an elongate element coupled to the support shaft, the elongate element having a first end and a second end, at least one of the first end and the second end being movable relative to the other end to change a size of a loop formed at least in part by the elongate element, the loop being movable from a collapsed position toward a fully expanded position, wherein, when the loop is in the collapsed position, the loop and a distal end of the support shaft are sized and shaped to be introduced into an anterior chamber of the eye, and wherein, when the loop is in the fully expanded position, the loop is sized and shaped to be positioned around the lens between the lens and the capsular bag, and wherein tensioning the loop reduces the size of the loop from the fully expanded position toward the collapsed position to cut the lens, wherein the elongate element has a polymer elbow at the first end having a non-circular cross-section, the elbow extending from an opening of the support shaft when the loop is in the fully expanded position so that the elbow deflects proximal of the opening, and wherein the elongate element forms the loop so that a loop plane is defined in the fully expanded position, wherein the loop plane is a plane selected so as to maximize an area bounded from the plane by the loop in the fully expanded position, wherein the elbow is at least twice as bendable for a force applied to a tip of the elbow and lying in the loop plane compared to a transverse force applied to the tip of the elbow and directed transverse to the loop plane.

2. The device of claim 1, wherein the second end of the elongate element is configured to be uncoupled and released from the support shaft, wherein uncoupling and release of the second end from the support shaft permits withdrawal of the second end from the eye.

3. The device of claim 1, wherein the elbow of the elongate element is crimped to form a living hinge.

4. The device of claim 1, wherein the elongate element is formed with the elbow being spaced apart from the support shaft, wherein the elbow is configured to be deflected toward the support shaft by rotating the support shaft about the longitudinal axis and engaging the lens when rotating.

5. The device of claim 1, wherein the elongate element is formed with the elbow having an unbiased position relative to the support shaft when the loop is in the fully expanded position, the tip of the elbow having an orientation at the tip which is 90-180 degrees from a distal orientation of the support shaft when the loop is in the fully expanded position, the distal orientation being a direction from the proximal end to the distal end of the support shaft.

6. The device of claim 1, wherein the elongate element has an unshaped portion and a pre-shaped portion when the loop is in the fully expanded position, the second end of the elongate element being movable relative to the support shaft to change the size of the loop, the elongate element having a first half extending from the first end to a midpoint and a second half extending from the second end to the midpoint when the loop is in the fully expanded position, the elongate element having a total length defined by an exposed length of the elongate element when the loop is in the fully expanded position.

7. The device of claim 1, wherein the support shaft includes a first tube having an angled tip that is angled to the longitudinal axis, the angled tip having a proximal portion that extends along the longitudinal axis and a distal portion which extends distally from the proximal portion and terminates at a distal end of the angled tip, the proximal portion having a proximal orientation and the distal portion having a distal orientation defined by a proximal axis and a distal axis, respectively, along which a first lumen extends in the proximal portion of the first tube, the proximal orientation and the distal orientation lying in and defining a working plane.

8. The device of claim 7, wherein the angled tip is formed so that the distal end of the angled tip configured to be is directed away from the loop when the loop is in the fully expanded position around the lens and the loop plane is perpendicular to a midplane of the lens.

9. The device of claim 1, further comprising:
a phacoemulsification device with the support shaft being a tip of the phacoemulsification device, the phacoemulsification device having a housing with the tip extending from the housing to the distal end of the support shaft, the tip being coupled to a vibrating element mounted to the housing for vibrating the tip, a first lumen extends through the tip and has an opening at the distal end of the tip, wherein the first lumen is coupled to a suction source to aspirate lens fragments through the first lumen.

10. The device of claim 9, wherein the elongate element extends from the tip of the phacoemulsification device when the loop moves toward the fully expanded position.

11. The device of claim 9, wherein the tip includes a first tube which extends to the distal end, the first tube having the first lumen, the tip also including a second tube positioned around the first tube, the second tube having a second lumen, the elongate element being movable outwardly to extend from the tip.

12. The device of claim 11, wherein the second lumen forms a space between the first tube and the second tube; and
the elongate element extending through the space and being removable from the eye by withdrawing the elongate element into the space.

13. The device of claim 1, further comprising:
a phacoemulsification hand piece having a lumen; and
a fluid Y-arm having a main lumen which splits into a first leg and a second leg, the main lumen being coupled to the lumen in the phacoemulsification hand piece.

14. The device of claim 1, wherein the support shaft comprises at least one lumen between the proximal end and the distal end of the support shaft, wherein the elongate element is removable from the at least one lumen of the support shaft by withdrawing the elongate element proximally relative to the support shaft so that the elongate element is not positioned within the at least one lumen.

15. The device of claim 14, wherein the device further comprises an actuator, wherein at least one end of the elongate element is coupled to the actuator so as to be released from its coupling during use of the device.

16. The device of claim 14, wherein the at least one lumen is in fluid communication with a suction source and/or an irrigation source.

* * * * *